US012397051B2

(12) United States Patent
Nag et al.

(10) Patent No.: US 12,397,051 B2
(45) Date of Patent: Aug. 26, 2025

(54) VACCINE FOR USE AGAINST CORONAVIRUS AND VARIANTS THEREOF

(71) Applicant: Globe Biotech Limited, Dacca (BD)

(72) Inventors: Kakon Nag, Dacca (BD); Juwel Chandra Baray, Dacca (BD); Maksudur Rahman Khan, Dacca (BD); Asif Mahmud, Dacca (BD); Enamul Haq Sarker, Dacca (BD); Samir Kumar, Dacca (BD); Jikrul Islam, Dacca (BD); Rony Roy, Dacca (BD); Mohammad Mohiuddin, Dacca (BD); Naznin Sultana, Dacca (BD)

(73) Assignee: Globe Biotech Limited, Dacca (BD)

(*) Notice: Subject to any disclaimer, the term of this patent is extended or adjusted under 35 U.S.C. 154(b) by 165 days.

(21) Appl. No.: 17/475,001

(22) Filed: Sep. 14, 2021

(65) Prior Publication Data
US 2023/0084012 A1    Mar. 16, 2023

(51) Int. Cl.
| | |
|---|---|
| *A61K 39/215* | (2006.01) |
| *A61K 9/1272* | (2025.01) |
| *A61K 9/51* | (2006.01) |
| *A61K 39/00* | (2006.01) |
| *A61K 48/00* | (2006.01) |

(52) U.S. Cl.
CPC .......... *A61K 39/215* (2013.01); *A61K 9/1272* (2013.01); *A61K 9/5123* (2013.01); *A61K 39/00* (2013.01); *A61K 48/0066* (2013.01); *A61K 48/0075* (2013.01); *A61K 2039/55555* (2013.01)

(58) Field of Classification Search
CPC .. A61K 39/215; A61K 9/1272; A61K 9/5123; A61K 39/00; A61K 48/0066; A61K 48/0075; A61K 2039/55555; A61K 2039/51; A61K 2039/57; A61K 2039/575; A61K 9/127; A61K 39/12; A61P 31/14; C07K 14/005; C12N 15/88; C12N 2770/20022; C12N 2770/20034
See application file for complete search history.

(56) References Cited

U.S. PATENT DOCUMENTS

| | | | |
|---|---|---|---|
| 2002/0123099 A1* | 9/2002 | Weiner | A61P 9/00 702/19 |
| 2022/0202930 A1* | 6/2022 | Roth | A61K 9/5123 |
| 2022/0370599 A1* | 11/2022 | Abshire | A61P 31/16 |
| 2022/0381780 A1* | 12/2022 | Wohlstadter | G16B 25/10 |
| 2022/0401550 A1* | 12/2022 | Simon-Loriere | C07K 14/005 |
| 2023/0285539 A1* | 9/2023 | Joyce | A61K 39/12 |
| 2023/0346921 A1* | 11/2023 | Wei | A61P 31/14 |
| 2024/0100151 A1* | 3/2024 | Carfi | A61K 39/215 |
| 2024/0139309 A1* | 5/2024 | Carfi | C07K 14/005 |
| 2024/0156946 A1* | 5/2024 | Roth | A61K 9/5123 |
| 2024/0342269 A1* | 10/2024 | Dias | A61K 9/5123 |

FOREIGN PATENT DOCUMENTS

WO    WO-2021226436 A1 * 11/2021 ........... A61K 39/215

OTHER PUBLICATIONS

Nag K, Chandra Baray J, Rahman Khan M, Mahmud A, Islam J, Myti S, Ali R, Haq Sarker E, Kumar S, Hossain Chowdhury M, Roy R, Islam F, et al. An mRNA-based vaccine candidate against SARS-CoV-2 elicits stable immuno-response with single dose. Vaccine. Jun. 23, 2021;39(28):3745-3755. Epub May 18, 2021. (Year: 2021).*
De Breyne S, Vindry C, Guillin O, Condé L, Mure F, Gruffat H, Chavatte L, Ohlmann T. Translational control of coronaviruses. Nucleic Acids Res. Dec. 16, 2020;48(22):12502-12522. (Year: 2020).*
Park JW, Lagniton PNP, Liu Y, Xu RH. mRNA vaccines for COVID-19: what, why and how. Int J Biol Sci. Apr. 10, 2021;17(6):1446-1460. doi: 10.7150/ijbs.59233. PMID: 33907508; PMCID: PMC8071766. (Year: 2021).*
Granados-Riveron JT, Aquino-Jarquin G. Engineering of the current nucleoside-modified mRNA-LNP vaccines against SARS-CoV-2. Biomed Pharmacother. Oct. 2021;142:111953. doi: 10.1016/j.biopha. 2021.111953. Epub Jul. 23, 2021. PMID: 34343897; PMCID: PMC8299225. (Year: 2021).*
Zhang Y, Zhang T, Fang Y, Liu J, Ye Q, Ding L. SARS-CoV-2 spike L452R mutation increases Omicron variant fusogenicity and infectivity as well as host glycolysis. Signal Transduct Target Ther. Mar. 9, 2022;7(1):76. (Year: 2022).*
Plante JA, Liu Y, Liu J, Xia H, Johnson BA, Lokugamage KG, Zhang X, Muruato AE, Zou J, Fontes-Garfias CR, Mirchandani D, Scharton D, Bilello JP, et al. Spike mutation D614G alters SARS-CoV-2 fitness. Nature. Apr. 2021;592(7852):116-121. Epub Oct. 26, 2020. Erratum in: Nature. Jul. 2021;595(7865): E1. (Year: 2020).*
Kumar R, Srivastava Y, Muthuramalingam P, Singh SK, Verma G, Tiwari S, Tandel N, Beura SK, Panigrahi AR, Maji S, Sharma P, Rai PK, Prajapati DK, Shin H, Tyagi RK. Understanding Mutations in Human SARS-CoV-2 Spike Glycoprotein: A Systematic Review & Meta-Analysis. Viruses. Mar. 27, 2023;15(4):856. (Year: 2023).*
VanInsberghe D, Neish AS, Lowen AC, Koelle K. Recombinant SARS-COV-2 genomes are currently circulating at low levels. bioRxiv [Preprint]. Mar. 15, 2021:2020.08.05.238386. Update in: Virus Evol. Jul. 15, 2021;7(2):veab059. (Year: 2021).*
Amendola A, et al. Surface glycoprotein, partial [Severe acute respiratory syndrome coronavirus 2]. GenBank: QVK80293.1., Aug. 9, 2021. (Year: 2021).*

* cited by examiner

*Primary Examiner* — Rachel B Gill
(74) *Attorney, Agent, or Firm* — Husch Blackwell LLP

(57) ABSTRACT

A novel transgene for use to produce a coronavirus vaccine is provided. The transgene encodes: i) an RNA polymerase promoter; ii) a 5' UTR; iii) a secretory sequence; iv) a coronavirus spike protein component, wherein the spike protein component incorporates a variant sequence at amino acid position 614 of a native spike protein; and v) a 3' UTR and poly A sequence. A vaccine is also provided comprising the transgene or an mRNA transcript thereof.

30 Claims, 12 Drawing Sheets
Specification includes a Sequence Listing.

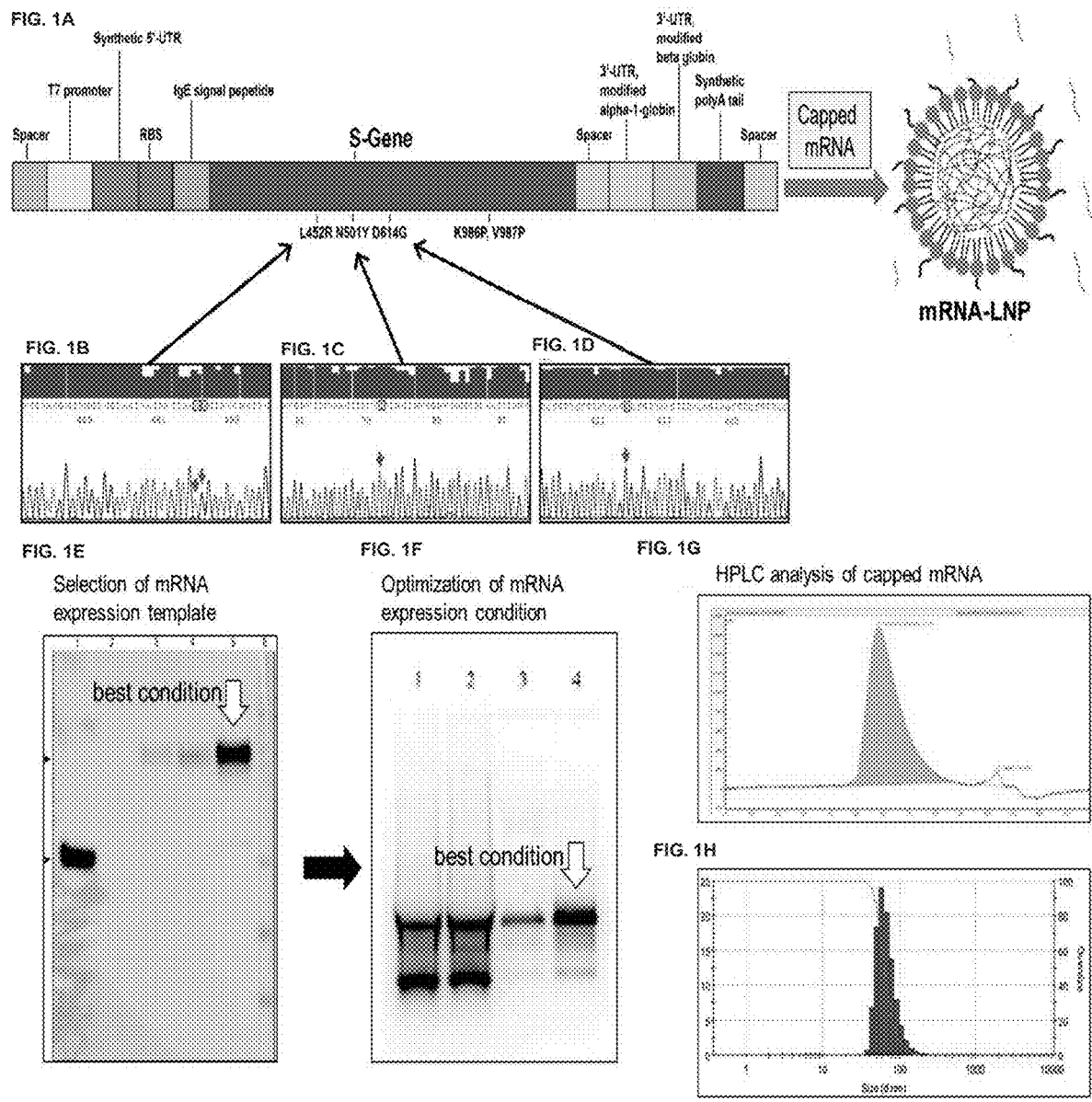

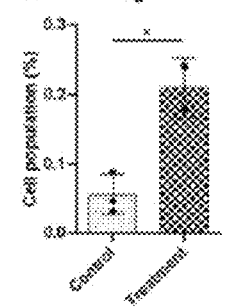 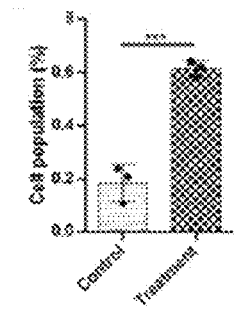 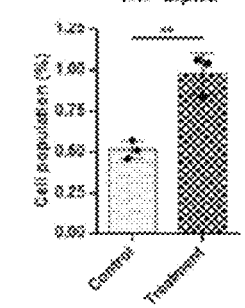 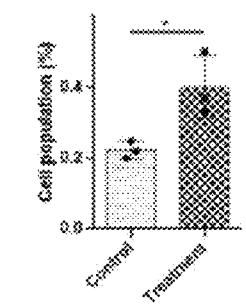
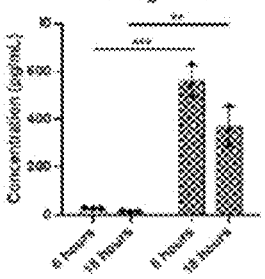 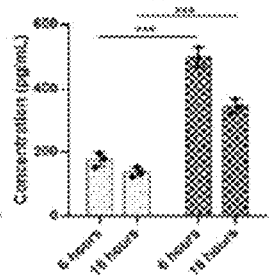 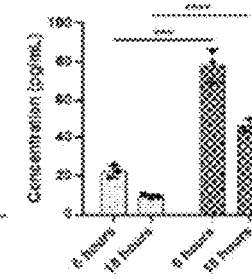 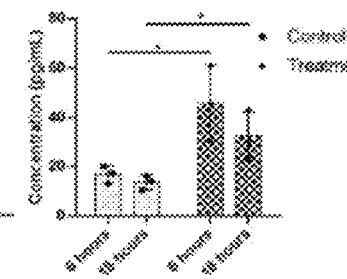
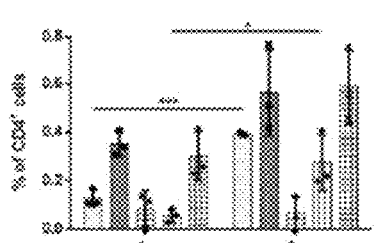 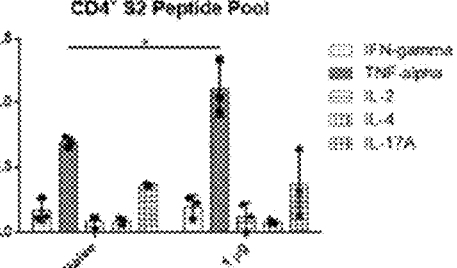
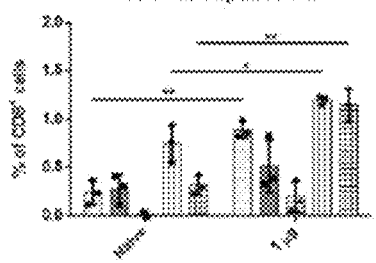 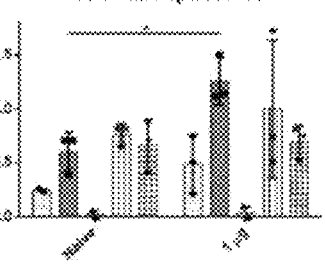 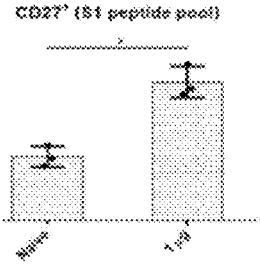

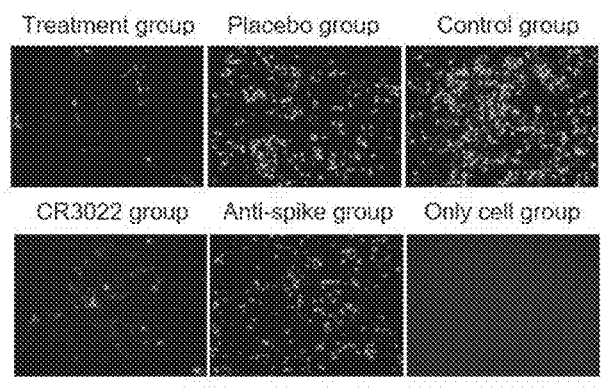
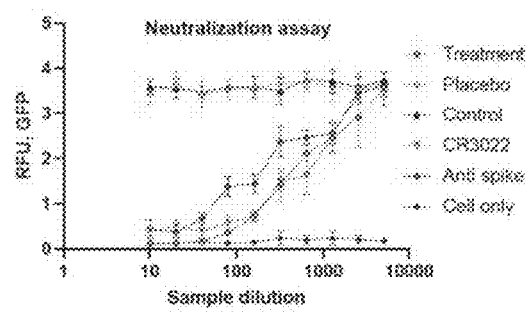
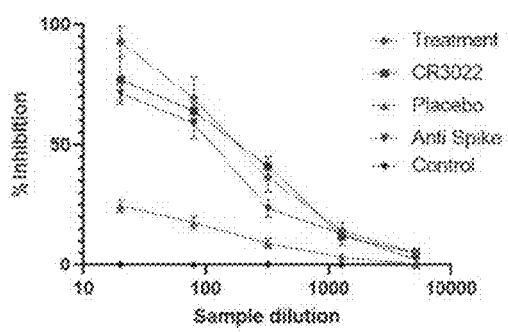
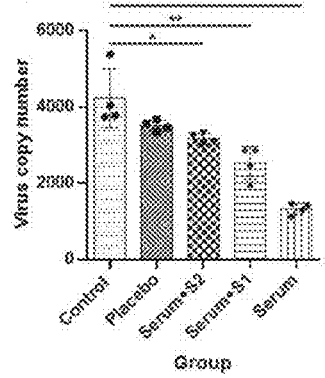
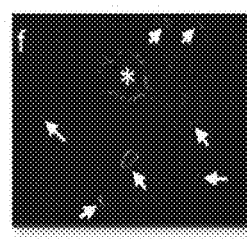
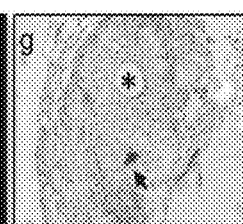
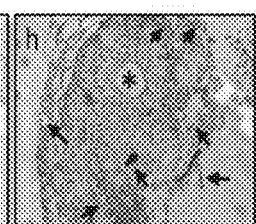
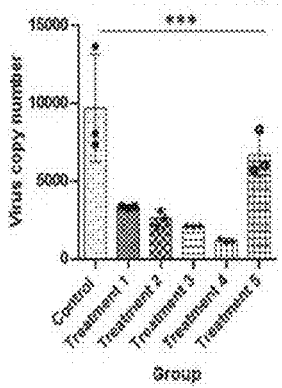
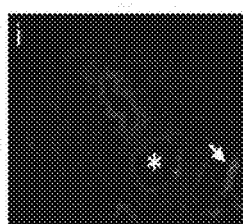
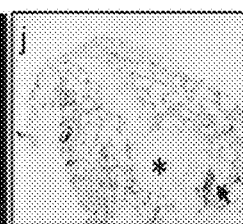
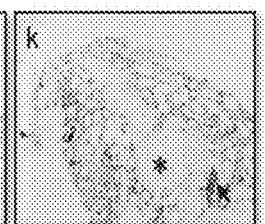

FIG. 5A)

| | | |
|---|---|---|
| 148 | cagtgtgttaatcttacaaccagaactcaattaccccctgcatacactaattctttcacacgtggtgttt | 217 |
| 218 | attaccctgacaaagttttcagatcctcagttttacattcaactcaggacttgttcttacctttcttttc | 287 |
| 288 | caatgttacttggttccatgctatacatgtctctgggaccaatggtactaagaggtttgataaccctgtc | 357 |
| 358 | ctaccatttaatgatggtgtttattttgcttccactgagaagtctaacataataagaggctggattttg | 427 |
| 428 | gtactactttagattcgaagacccagtccctacttattgtaataacgctactaatgttgttattaaagt | 497 |
| 498 | ctgtgaatttcaattttgtaatgatccattttgggtgtttattaccacaaaaacaacaaaagttggatg | 567 |
| 568 | gaaagtgagttcagagtttattctagtgcgaataattgcacttttgaatatgtctctcagccttttctta | 637 |
| 638 | tggaccttgaaggaaaacaggggtaatttcaaaaatcttagggaatttgtgtttaagaatattgatggtta | 707 |
| 708 | ttttaaaatatattctaagcacacgcctattaatttagtgcgtgatctccctcagggttttcggcttta | 777 |
| 778 | gaaccattggtagatttgccaataggtattaacatcactaggtttcaaactttacttgctttacatagaa | 847 |
| 848 | gttatttgactcctggtgattcttcttcaggttggacagctggtgctgcagcttatatgtgggttatct | 917 |
| 918 | tcaacctaggactttctattaaaatataatgaaaatggaaccattacagatgctgtagactgtgcactt | 987 |
| 988 | gaccctctctcagaaacaaagtgtacgttgaaatccttcactgtagaaaaaggaatctatcaaacttcta | 1057 |
| 1058 | actttagagtccaaccaacagaatctattgttagatttcctaatattacaaacttgtgccctttggtga | 1127 |
| 1128 | agtttttaacgccaccagatttgcatctgtttatgcttggaacaggaagagaatcagcaactgtgttgct | 1197 |
| 1198 | gattattctgtcctatataattccgcatcattttccacttttaagtgttatggagtgtctcctactaaat | 1267 |
| 1268 | taaatgatctctgctttactaatgtctatgcagattcatttgtaattagaggtgatgaagtcagacaaat | 1337 |
| 1338 | cgctccagggcaaactggaaagattgctgattataattataaaattaccagatgattttacaggctgcgtt | 1407 |
| 1408 | atagcttggaattctaacaatcttgattctaaggttggtggtaattataattacctgtatagattgtta | 1477 |
| 1478 | ggaagtcaatctcaaaccttttgagagagatatttcaactgaaatctatcaggccggtagcacaccttg | 1547 |
| 1548 | taatggtgttgaaggttttaattgttacttccttacaatcatatggtttccaacccactaatggtgtt | 1617 |
| 1618 | ggttaccaaccatacagagtagtagtactttcttttgaacttctacatgcaccagcaactgtttgtggac | 1687 |
| 1688 | ctaaaaagtctactaatttggttaaaaacaaatgtgtcaatttcaacttcaatggtttaacaggcacagg | 1757 |
| 1758 | tgttcttactgagtctaacaaaaagtttctgcctttccaacaatttggcagagacattgctgacactact | 1827 |
| 1828 | gatgctgtccgtgatccacagacacttgagattcttgacattacaccatgttcttttggtggtgtcagtg | 1897 |
| 1898 | ttataacaccaggaacaaatacttctaaccaggttgctgttctttatcagggtgttaactgcacagaagt | 1967 |
| 1968 | ccctgttgctattcatgcagatcaacttactcctacttggcgtgtttattctacaggttctaatgtttttt | 2037 |
| 2038 | caaacacgtgcaggctgtttaatagggggctgaacatgtcaacaactcatatgagtgtgacatacccattg | 2107 |
| 2108 | gtgcaggtatatgcgctagttatcagactcagactaattctcctcggcgggcacgtagtgtagctagtca | 2177 |
| 2178 | atccatcattgcctacactatgtcacttggtgcagaaaattcagttgcttactctaataactctattgcc | 2247 |
| 2248 | atacccacaaattttactattagtgttaccacagaaattctaccagtgtctatgaccaagacatcagtag | 2317 |
| 2318 | attgtacaatgtacatttgtggtgattcaactgaatgcagcaatcttttgttgcaatatggcagttttg | 2387 |
| 2388 | tacacaattaaaccgtgctttaactggaatagctgttgaacaagacaaaaacacccaagaagttttgca | 2457 |
| 2458 | caagtcaaacaaatttacaaaacaccaccaattaaagattttggtggttttaattttcacaaatattac | 2527 |
| 2528 | cagatccatcaaaaccaagcaagaggtcattattgaagatctacttttcaacaaagtgacacttgcaga | 2597 |
| 2598 | tgctggcttcatcaaacaatatggtgattgccttggtgatattgctgctagagacctcattgtgcacaa | 2667 |
| 2668 | aagtttaacggccttactgttttgccacctttgctcacagatgaaatgattgctcaatacacttctgcac | 2737 |
| 2738 | tgttagcgggtacaatcacttctggttggacctttggtgcaggtgctgcattacaaataccatttgctat | 2807 |
| 2808 | gcaaatggcttataggtttaatggtattggagttacacagaatgttctctatgagaaccaaaaattgatt | 2877 |
| 2878 | gccaaccaatttaatagtgctattggcaaaattcaagactcactttcttccacagcaagtgcacttggaa | 2947 |
| 2948 | aacttcaagatgtggtcaaccaaaatgcacaagctttaaacacgcttgttaaacaacttagctccaattt | 3017 |
| 3018 | tggtgcaatttcaagtgttttaaatgatatcctttcacgtcttgaccctcctgaggctgaagtgcaaatt | 3087 |
| 3088 | gataggttgatcacaggcagacttcaaagtttgcagacatatgtgactcaacaattaattagagctgcag | 3157 |
| 3158 | aaatcagagcttctgctaatcttgctgctactaaaatgtcagagtgtgtacttggacaatcaaaaagagt | 3227 |
| 3228 | tgattttgtggaaagggctatcatcttatgtccttccctcagtcagcacctcatggtgtagtcttcttg | 3297 |
| 3298 | catgtgacttatgtccctgcacaagaaaagaacttcacaactgctcctgccattgtcatgatggaaaag | 3367 |

FIGURE 5 cont'd

| 3368 | cacactttcctcgtgaaggtgtctttgtttcaaatggcacacactggtttgtaacacaaaggaattttta | 3437 |
| 3438 | tgaaccacaaatcattactacagacaacacatttgtgtctggtaactgtgatgttgtaataggaattgtc | 3507 |
| 3508 | aacaacacagtttatgatcctttgcaacctgaattagactcattcaaggaggagttagataaatatttta | 3577 |
| 3578 | agaatcatacatcaccagatgttgatttaggtgacatctctggcattaatgcttcagttgtaaacattca | 3647 |
| 3648 | aaaagaaattgaccgcctcaatgaggttgccaagaatttaaatgaatctctcatcgatctccaagaactt | 3717 |
| 3718 | ggaaagtatgagcagtatataaaatggccatggtacatttggctaggttttatagctggcttgattgcca | 3787 |
| 3788 | tagtaatggtgacaattatgctttgctgtatgaccagttgctgtagttgtctcaagggctgttgttcttg | 3857 |
| 3858 | tggatcctgctgcaaatttgatgaagacgactctgagccagtgctcaaaggagtcaaattacattacaca | 3927 |
| 3928 | taa (SEQ ID NO: 8) | 3930 |

FIG. 5B)

| 148 | cagtgcgtgaacctgaccaccagaacacagctgcctccagcctacaccaacagcttcaccagaggcgtgt | 217 |
| 218 | actaccccgacaaggtgttcagatccagcgtgctgcactctacccaggacctgttcctgcctttcttcag | 287 |
| 288 | caacgtgacctggttccacgccatccacgtgtccggcaccaatggcaccaagagattcgacaaccccgtg | 357 |
| 358 | ctgcccttcaacgacggggtgtactttgccagcaccgagaagtccaacatcatcagaggctggatcttcg | 427 |
| 428 | gcaccacactggacagcaagacccagagcctgctgatcgtgaacaacgccaccaacgtggtcatcaaagt | 497 |
| 498 | gtgcgagttccagttctgcaacgaccccttcctgggcgtctactaccaagaacaacaagagctggatg | 567 |
| 568 | gaaagcgagttccgggtgtacagcagcgccaacaactgcaccttcgagtacgtgtcccagcctttcctga | 637 |
| 638 | tggacctggaaggcaagcagggcaacttcaagaacctgcgcgagttcgtgttcaagaacatcgacggcta | 707 |
| 708 | cttcaagatctacagcaagcacacccctatcaacctcgtgcgggatctgcctcagggcttctctgctctg | 777 |
| 778 | gaacccctggtggatctgcccatcggcatcaacatcacccggtttcagacactgctggccctgcacagaa | 847 |
| 848 | gctacctgacacctggcgatagcagctctggatggacagctggagccgctgcctactatgtgggatacct | 917 |
| 918 | gcagcctcggaccttcctgctgaagtacaacgagaacggcaccatcaccgacgccgtggattgtgctctg | 987 |
| 988 | gatcctctgagcgagacaaagtgcaccctgaagtccttcaccgtggaaaagggcatctaccagaccagca | 1057 |
| 1058 | acttccgggtgcagcccaccgaatccatcgtgcggttccccaatatcaccaatctgtgcccccttcggcga | 1127 |
| 1128 | ggtgttcaatgccaccagattcgcctctgtgtacgcctggaaccggaagcggatcagcaattgcgtggcc | 1197 |
| 1198 | gactactccgtgctgtacaactccgccagcttcagcaccttcaagtgctacggcgtgtcccctaccaagc | 1267 |
| 1268 | tgaacgacctgtgcttcacaaacgtgtacgccgacagcttcgtgatccggggagatgaagtgcggcagat | 1337 |
| 1338 | tgcccctggacagacaggcaagatcgccgactacaactacaagctgcccgacgacttcaccggctgtgtg | 1407 |
| 1408 | attgctggaacagcaacaacctggactccaaagtcggcggcaactacaattacctgtaccggctgttcc | 1477 |
| 1478 | ggaagtccaatctgaagcccttcgagcgggacatctccaccgagatctatcaggccggcagcaccccttg | 1547 |
| 1548 | taacggcgtggaaggcttcaactgctactttccactgcagtcctacggcttccagccaacaaacggcgtg | 1617 |
| 1618 | ggctaccagcettacagagtggtggtgctgagcttcgagctgctgcatgctcctgccacagtgtgcggcc | 1687 |
| 1688 | ctaagaaaagcaccaatctcgtgaagaacaaatgcgtgaacttcaacttcaacggcctgaccggcaccgg | 1757 |
| 1758 | cgtgctgacagagagcaacaagaagttcctgccattccagcagttcggccgggatatcgccgataccaca | 1827 |
| 1828 | gatgccgtcagagatccccagacactggaaatcctggacatcacccttgcagcttcggcggagtgtctg | 1897 |
| 1898 | tgatcaccctggcaccaacaccagcaatcaggtggcagtgctgtaccaggatgtgaactgtacagaggt | 1967 |
| 1968 | gccagtggccattcacgccgatcagctgacccctacttggcgggtgtactccacaggcagcaatgtgttt | 2037 |
| 2038 | cagaccagagccggctgtctgatcggagccgagcacgtgaacaatagctacgagtgcgacatccccatcg | 2107 |
| 2108 | gcgctggcatctgcgcctcttaccagacacagacaaacagccccagacgggccagatctgtggccagcca | 2177 |
| 2178 | gagcatcattgcctacacaatgtctctgggagccgagaacagcgtggcctactccaacaactctatcgct | 2247 |
| 2248 | atccccaccaacttcaccatcagcgtgaccacagagatcctgcctgtgtccatgaccaagaccagcgtgg | 2317 |
| 2318 | actgcaccatgtacatctgcggcgattccaccgagtgctccaacctgctgctgcagtacggcagcttctg | 2387 |
| 2388 | cacccagctgaatagagccctgacagggatcgccgtggaacaggacaagaacacccaagaggtgttcgcc | 2457 |
| 2458 | caagtgaagcagatctacaagaccccctccatcaaggacttcggcggcttcaatttcagccagattctgc | 2527 |

FIGURE 5 cont'd

| | | |
|---|---|---|
| 2528 | ccgatcctagcaagcccagcaagcggagcttcatcgaggacctgctgttcaacaaagtgacactggccga | 2597 |
| 2598 | cgccggcttcatcaagcagtatggcgattgtctgggcgacattgccgccagggatctgatttgcgcccag | 2667 |
| 2668 | aagtttaacggactgacagtgctgcctcctctgctgaccgatgagatgatcgcccagtacacatctgccc | 2737 |
| 2738 | tgctggccggcacaatcacaagcggctggacatttggagctggcgctgccctgcagatcccctttgctat | 2807 |
| 2808 | gcagatggcctaccggttcaacggcatcggagtgacccagaatgtgctgtacgagaaccagaagctgatc | 2877 |
| 2878 | gccaaccagttcaacagcgccatcggcaagatccaggacagcctgagcagcacagcaagcgccctgggaa | 2947 |
| 2948 | agctgcaggacgtggtcaaccagaatgcccaggcactgaacaccctggtcaagcagctgtctagcaactt | 3017 |
| 3018 | cggagccatcagctctgtgctgaacgatatcctgagcagactggaccctcctgaggccgaggtgcagatc | 3087 |
| 3088 | gacagactgatcacaggcagactgcagagcctccagacatacgtgacccagcagctgatcagagccgccg | 3157 |
| 3158 | agattagagcctctgccaatctggccgccaccaagatgtctgagtgtgtgctgggccagagcaagagagt | 3227 |
| 3228 | ggacttttgcggcaagggctaccacctgatgagcttccctcagtctgcaccacacggcgtggtgtttctg | 3297 |
| 3298 | cacgtgacctacgtgcccgctcaagagaagaatttcaccaccgctccagccatctgccacgacggcaaag | 3367 |
| 3368 | cccactttcctagagaaggcgtgttcgtgtccaacggcacccattggttcgtgacacagcggaacttcta | 3437 |
| 3438 | cgagcccagatcatcaccaccgacaacaccttcgtgtctggcaactgcgacgtcgtgatcggcattgtg | 3507 |
| 3508 | aacaataccgtgtacgaccctctgcagcccgagctggacagcttcaaagaggaactggacaagtacttta | 3577 |
| 3578 | agaaccacacaagccccgacgtggacctgggcgatatcagcggaatcaatgccagcgtcgtgaacatcca | 3647 |
| 3648 | gaaagagatcgaccggctgaacgaggtggccaagaatctgaacgagagcctgatcgacctgcaagaactg | 3717 |
| 3718 | gggaagtacgagcagtacatcaagtggccttggtacatctggctgggctttatcgccggactgattgcca | 3787 |
| 3788 | tcgtgatggtcacaatcatgctgtgttgcatgaccagctgctgtagctgcctgaagggctgttgtagctg | 3857 |
| 3858 | tggctcctgctgcaagttcgacgaggacgattctgagcccgtgctgaaaggcgtgaagctgcactacacc | 3927 |
| 3928 | tga (SEQ ID NO: 9) | 3930 |

FIG. 5C)

| | | |
|---|---|---|
| 148 | cagtgcgtgaacctgaccaccagaacacagctgcctccagcctacaccaacagcttcaccagaggcgtgt | 217 |
| 218 | actaccccgacaaggtgttcagatccagcgtgctgcactctacccaggacctgttcctgcctttcttcag | 287 |
| 288 | caacgtgacctggttccacgccatccacgtgtccggcaccaatggcaccaagagattcgacaaccccgtg | 357 |
| 358 | ctgcccttcaacgacggggtgtactttgccagcaccgagaagtccaacatcatcagagggctggatcttcg | 427 |
| 428 | gcaccacactggacagcaagacccagagcctgctgatcgtgaacaacgccaccaacgtggtcatcaaagt | 497 |
| 498 | gtgcgagttccagttctgcaacgaccccttcctgggcgtctactaccacaagaacaacaagagctggatg | 567 |
| 568 | gaaagcgagttccgggtgtacagcagcgccaacaactgcaccttcgagtacgtgtcccagccttttcctga | 637 |
| 638 | tggacctggaaggcaagcagggcaacttcaagaacctgcgcgagttcgtgttcaagaacatcgacggcta | 707 |
| 708 | cttcaagatctacagcaagcacacccctatcaacctcgtgcgggatctgcctcaggcttctctgctctg | 777 |
| 778 | gaaccctggtggatctgcccatcggcatcaacatcacccggtttcagacactgctggccctgcacagaa | 847 |
| 848 | gctacctgacacctggcgatagcagctctggatggacagctggagccgctgcctactatgtgggatacct | 917 |
| 918 | gcagcctcggaccttcctgctgaagtacaacgagaacggccaccatcaccgacgccgtggattgtgctctg | 987 |
| 988 | gatcctctgagcgagacaaagtgcacctgaagtccttcaccgtggaaaagggcatctaccagaccagca | 1057 |
| 1058 | acttccgggtgcagcccaccgaatccatcgtgcggttccccaatatcaccaatctgtgccccttcggcga | 1127 |
| 1128 | ggtgttcaatgccaccagattcgcctctgtgtacgcctggaaccggaagcggatcagcaattgcgtggcc | 1197 |
| 1198 | gactactccgtgctgtacaactccgccagcttcagcaccttcaagtgctacggcgtgtcccctaccaagc | 1267 |
| 1268 | tgaacgacctgtgcttcacaaacgtgtacgccgacagcttcgtgatccggggagatgaagtgcggcagat | 1337 |
| 1338 | tgcccctggacagacaggcaagatcgccgactacaactacaagctgcccgacgacttcaccggctgtgtg | 1407 |
| 1408 | attgcctggaacagcaacaacctggactccaaagtcggcggcaactacaattacctgtaccggctgttcc | 1477 |
| 1478 | ggaagtccaatctgaagcccttcgagcgggacatctccaccgagatctatcaggccggcagcacccttg | 1547 |
| 1548 | taacggcgtggaaggcttcaactgctacttcccactgcagtcctacggcttccagccaacaaacggcgtg | 1617 |
| 1618 | ggctaccagccttacagagtggtggtgctgagcttcgagctgctgcatgctcctgccacagtgtgcggcc | 1687 |
| 1688 | ctaagaaaagcaccaatctcgtgaagaacaaatgcgtgaacttcaacttcaacggcctgaccggcaccgg | 1757 |

FIGURE 5 cont'd

| | | |
|---|---|---|
| 1758 | cgtgctgacagagagcaacaagaagttcctgccattccagcagttcggccgggatatcgccgataccaca | 1827 |
| 1828 | gatgccgtcagagatccccagacactggaaatcctggacatcacccccttgcagcttcggcggagtgtctg | 1897 |
| 1898 | tgatcacccctggcaccaacaccagcaatcaggtggcagtgctgtaccagggcgtgaactgtacagaggt | 1967 |
| 1968 | gccagtggccattcacgccgatcagctgacccctacttggcgggtgtactccacaggcagcaatgtgttt | 2037 |
| 2038 | cagaccagagccggctgtctgatcggagccgagcacgtgaacaatagctacgagtgcgacatccccatcg | 2107 |
| 2108 | gcgctggcatctgcgcctcttaccagacacagacaaacagccccagacggggccagatctgtggccagcca | 2177 |
| 2178 | gagcatcattgcctacacaatgtctctgggagccgagaacagcgtggcctactccaacaactctatcgct | 2247 |
| 2248 | atccccaccaacttcaccatcagcgtgaccacagagatcctgcctgtgtccatgaccaagaccagcgtgg | 2317 |
| 2318 | actgcaccatgtacatctgcggcgattccaccgagtgctccaacctgctgctgcagtacggcagcttctg | 2387 |
| 2388 | cacccagctgaatagagccctgacagggatcgccgtggaacaggacaagaacacccaagaggtgttcgcc | 2457 |
| 2458 | caagtgaagcagatctacaagacccctcctatcaaggacttcggcggcttcaatttcagccagattctgc | 2527 |
| 2528 | ccgatcctagcaagcccagcaagcggagcttcatcgaggacctgctgttcaacaaagtgacactggccga | 2597 |
| 2598 | cgccggcttcatcaagcagtatggcgattgtctgggcgacattgccgccagggatctgatttgcgcccag | 2667 |
| 2668 | aagtttaacggactgacagtgctgcctcctctgctgaccgatgagatgatcgcccagtacacatctgccc | 2737 |
| 2738 | tgctggccggcacaatcacaagcggctggacatttggagctggcgctgccctgcagatccccttttgctat | 2807 |
| 2808 | gcagatggcctaccggttcaacggcatcggagtgacccagaatgtgctgtacgagaaccagaagctgatc | 2877 |
| 2878 | gccaaccagttcaacagcgccatcggcaagatccaggacagcctgagcagcacagcaagcgccctgggaa | 2947 |
| 2948 | agctgcaggacgtggtcaaccagaatgccCaggcactgaacaccctggtcaagcagctgtctagcaactt | 3017 |
| 3018 | cggagccatcagctctgtgctgaacgatatcctgagcagactggaccctcctgaggccgaggtgcagatc | 3087 |
| 3088 | gacagactgatcacaggcagactgcagagcctccagacatacgtgacccagcagctgatcagagccgcg | 3157 |
| 3158 | agattagagcctctgccaatctggccgccaccaagatgtctgagtgtgtgctgggccagagcaagagagt | 3227 |
| 3228 | ggactttttgcggcaagggctaccacctgatgagcttccctcagtctgcaccacacggcgtggtgtttctg | 3297 |
| 3298 | cacgtgacctacgtgcccgctcaagagaagaatttcaccaccgctccagccatctgccacgacggcaaag | 3367 |
| 3368 | cccactttcctagagaaggcgtgttcgtgtccaacggcacccattggttcgtgacacagcggaacttcta | 3437 |
| 3438 | cgagccccagatcatcaccaccgacaacaccttcgtgtctggcaactgcgacgtcgtgatcggcattgtg | 3507 |
| 3508 | aacaataccgtgtacgaccctctgcagcccgagctggacagcttcaaagaggaactggacaagtacttta | 3577 |
| 3578 | agaaccacacaagccccgacgtggacctgggcgatatcagcgggaatcaatgccagcgtcgtgaacatcca | 3647 |
| 3648 | gaaagagatcgaccggctgaacgaggtggccaagaatctgaacgagagcctgatcgacctgcaagaactg | 3717 |
| 3718 | gggaagtacgagcagtacatcaagtggccttggtacatctggctgggctttatcgccggactgattgcca | 3787 |
| 3788 | tcgtgatggtcacaatcatgctgtgttgcatgaccagctgctgtagctgcctgaagggctgttgtagctg | 3857 |
| 3858 | tggctcctgctgcaagttcgacgaggacgattctgagcccgtgctgaaaggcgtgaagctgcactacacc | 3927 |
| 3928 | tga (SEQ ID NO: 10) | 3930 |

FIG. 5D)

| | | |
|---|---|---|
| 148 | cagtgcgtgaacctgaccaccagaacacagctgcctccagcctacaccaacagcttcaccagaggcgtgt | 217 |
| 218 | actaccccgacaaggtgttcagatccagcgtgctgcactctacccaggacctgttcctgcccttcttcag | 287 |
| 288 | caacgtgacctggttccacgccatccacgtgtccggcaccaatggcaccaagagattcgacaaccccgtg | 357 |
| 358 | ctgcccttcaacgacggggtgtactttgccagcaccgagaagtccaacatcatcagaggctggatcttcg | 427 |
| 428 | gcaccacactggacagcaagacccagagcctgctgatcgtgaacaacgccaccaacgtggtcatcaaagt | 497 |
| 498 | gtgcgagttccagttctgcaacgaccccttcctgggcgtctactaccacaagaacaacaagagctggatg | 567 |
| 568 | gaaagcgagttccgggtgtacagcagcgccaacaactgcaccttcgagtacgtgtcccagcctttcctga | 637 |
| 638 | tggacctggaaggcaagcagggcaacttcaagaacctgcgcgagttcgtgttcaagaacatcgacggcta | 707 |
| 708 | cttcaagatctacagcaagcacacccctatcaacctcgtgcgggatctgcctcagggcttctctgctctg | 777 |
| 778 | gaacccctggtggatctgcccatcggcatcaacatcacccggtttcagacactgctggccctgcacagaa | 847 |
| 848 | gctacctgacacctggcgatagcagctctggatggacagcaggagccgctgcctactatgtgggatacct | 917 |
| 918 | gcagcctcggaccttcctgctgaagtacaacgagaacggcaccatcaccgacgccgtggattgtgctctg | 987 |

FIGURE 5 cont'd

| | | |
|---|---|---|
| 988 | gatcctctgagcgagacaaagtgcaccctgaagtccttcaccgtggaaaagggcatctaccagaccagca | 1057 |
| 1058 | acttccgggtgcagcccaccgaatccatcgtgcggttccccaatatcaccaatctgtgccccttcggcga | 1127 |
| 1128 | ggtgttcaatgccaccagattcgcctctgtgtacgcctggaaccggaagcggatcagcaattgcgtggcc | 1197 |
| 1198 | gactactccgtgctgtacaactccgccagcttcagcaccttcaagtgctacggcgtgtcccctaccaagc | 1267 |
| 1268 | tgaacgacctgtgcttcacaaacgtgtacgccgacagcttcgtgatccggggagatgaagtgcggcagat | 1337 |
| 1338 | tgcccctggacagacaggcaagatcgccgactacaactacaagctgcccgacgacttcaccggctgtgtg | 1407 |
| 1408 | attgcctggaacagcaacaacctggactccaaagtcggcggcaactacaattacagataccggctgttcc | 1477 |
| 1478 | ggaagtccaatctgaagcccttcgagcgggacatctccaccgagatctatcaggccggcagcacccttg | 1547 |
| 1548 | taacggcgtggaaggcttcaactgctacttcccactgcagtcctacggcttccagccaacatacggcgtg | 1617 |
| 1618 | ggctaccagcctacagagtggtggtgctgagcttcgagctgctgcatgctcctgccacagtgtgcggcc | 1687 |
| 1688 | ctaagaaaagcaccaatctcgtgaagaacaaatgcgtgaacttcaacttcaacggcctgaccggcaccgg | 1757 |
| 1758 | cgtgctgacagagagcaacaagaagttcctgccattccagcagttcggccgggatatcgccgataccaca | 1827 |
| 1828 | gatgccgtcagagatccccagacactggaaatcctggacatcaccccttgcagcttcggcggagtgtctg | 1897 |
| 1898 | tgatcacccctggcaccaacaccagcaatcaggtggcagtgctgtaccagggcgtgaactgtacagaggt | 1967 |
| 1968 | gccagtggccattcacgccgatcagctgacccctacttggcgggtgtactccacaggcagcaatgtgttt | 2037 |
| 2038 | cagaccagagccggctgtctgatcggagccgagcacgtgaacaatagctacgagtgcgacatccccatcg | 2107 |
| 2108 | gcgctggcatctgcgcctcttaccagacacagacaaacagccccagacggggccagatctgtggccagcca | 2177 |
| 2178 | gagcatcattgctacacaatgtctctgggagccgagaacagcgtggcctactccaacaactctatcgct | 2247 |
| 2248 | atccccaccaacttcaccatcagcgtgaccacagagatcctgcctgtgtccatgaccaagaccagcgtgg | 2317 |
| 2318 | actgcaccatgtacatctgcggcgattccaccgagtgctccaacctgctgctgcagtacggcagcttctg | 2387 |
| 2388 | cacccagctgaatagagccctgacagggatcgccgtggaacaggacaagaacacccaagaggtgttcgcc | 2457 |
| 2458 | caagtgaagcagatctacaagacccctcctatcaaggacttcggcggcttcaatttcagccagattctgc | 2527 |
| 2528 | ccgatcctagcaagcccagcaagcggagcttcatcgaggacctgctgttcaacaaagtgacactggccga | 2597 |
| 2598 | cgccggcttcatcaagcagtatggcgattgtctgggcgacattgccgccagggatctgatttgcgcccag | 2667 |
| 2668 | aagttaacggactgacagtgctgcctcctctgctgaccgatgagatgatcgcccagtacacatctgccc | 2737 |
| 2738 | tgctggccggcacaatcacaagcggctggacatttggagctggcgctgccctgcagatccccttgctat | 2807 |
| 2808 | gcagatggcctaccggttcaacggcatcggagtgacccagaatgtgctgtacgagaaccagaagctgatc | 2877 |
| 2878 | gccaaccagttcaacagcgccatcggcaagatccaggacagcctgagcagcacagcaagcgccctgggaa | 2947 |
| 2948 | agctgcaggacgtggtcaaccagaatgcccaggcactgaacacccctggtcaagcagctgtctagcaactt | 3017 |
| 3018 | cggagccatcagctctgtgctgaacgatatcctgagcagactggaccctcctgaggccgaggtgcagatc | 3087 |
| 3088 | gacagactgatcacaggcagactgcagagcctccagacatacgtgacccagcagctgatcagagccgccg | 3157 |
| 3158 | agattagagcctctgccaatctggccgccaccaagatgtctgagtgtgtgctgggccagagcaagagagt | 3227 |
| 3228 | ggacttttgcggcaagggctaccacctgatgagcttccctcagtctgcaccacacggcgtggtgtttctg | 3297 |
| 3298 | cacgtgacctacgtgcccgctcaagagaagaatttcaccaccgctccagccatctgccacgacggcaaag | 3367 |
| 3368 | cccactttcctagagaaggcgtgttcgtgtccaacggcacccattggttcgtgacacagcggaacttcta | 3437 |
| 3438 | cgagccccagatcatcaccaccgacaacaccttcgtgtctggcaactgcgacgtcgtgatcggcattgtg | 3507 |
| 3508 | aacaataccgtgtacgaccctctgcagcccgagctggacagcttcaaagaggaactggacaagtactta | 3577 |
| 3578 | agaaccacacaagccccgacgtggacctgggcgatatcagcggaatcaatgccagcgtcgtgaacatcca | 3647 |
| 3648 | gaaagagatcgaccggctgaacgaggtggccaagaatctgaacgagagcctgatcgacctgcaagaactg | 3717 |
| 3718 | gggaagtacgagcagtacatcaagtggccttggtacatctggctgggctttatcgccggactgattgcca | 3787 |
| 3788 | tcgtgatggtcacaatcatgctgtgttgcatgaccagctgctgtagctgcctgaagggctgttgtagctg | 3857 |
| 3858 | tggctcctgctgcaagttcgacgaggacgattctgagcccgtgctgaaaggcgtgaagctgcactacacc | 3927 |
| 3928 | tga (SEQ ID NO: 11) | 3930 |

FIG. 6A)

```
14   QCVNLTTRTQLPPAYTNSFTRGVYYPDKVFRSSVLHSTQDLFLPFFSNVT              64
64   WFHAIHVSGTNGTKRFDNPVLPFNDGVYFASTEKSNIIRGWIFGTTLDSK             113
114  TQSLLIVNNATNVVIKVCEFQFCNDPFLGVYYHKNNKSWMESEFRVYSSA             163
164  NNCTFEYVSQPFLMDLEGKQGNFKNLREFVFKNIDGYFKIYSKHTPINLV             213
214  RDLPQGFSALEPLVDLPIGINITRFQTLLALHRSYLTPGDSSSGWTAGAA             263
264  AYYVGYLQPRTFLLKYNENGTITDAVDCALDPLSETKCTLKSFTVEKGIY             313
314  QTSNFRVQPTESIVRFPNITNLCPFGEVFNATRFASVYAWNRKRISNCVA             363
364  DYSVLYNSASFSTFKCYGVSPTKLNDLCFTNVYADSFVIRGDEVRQIAPG             413
414  QTGKIADYNYKLPDDFTGCVIAWNSNNLDSKVGGNYNYLYRLFRKSNLKP             463
464  FERDISTEIYQAGSTPCNGVEGFNCYFPLQSYGFQPTNGVGYQPYRVVVL             513
514  SFELLHAPATVCGPKKSTNLVKNKCVNFNFNGLTGTGVLTESNKKFLPFQ             563
564  QFGRDIADTTDAVRDPQTLEILDITPCSFGGVSVITPGTNTSNQVAVLYQ             613
614  GVNCTEVPVAIHADQLTPTWRVYSTGSNVFQTRAGCLIGAEHVNNSYECD             663
664  IPIGAGICASYQTQTNSPRRARSVASQSIIAYTMSLGAENSVAYSNNSIA             713
714  IPTNFTISVTTEILPVSMTKTSVDCTMYICGDSTECSNLLLQYGSFCTQL             763
764  NRALTGIAVEQDKNTQEVFAQVKQIYKTPPIKDFGGFNFSQILPDPSKPS             813
814  KRSFIEDLLFNKVTLADAGFIKQYGDCLGDIAARDLICAQKFNGLTVLPP             863
864  LLTDEMIAQYTSALLAGTITSGWTFGAGAALQIPFAMQMAYRFNGIGVTQ             913
914  NVLYENQKLIANQFNSAIGKIQDSLSSTASALGKLQDVVNQNAQALNTLV             963
964  KQLSSNFGAISSVLNDILSRLDPPEAEVQIDRLITGRLQSLQTYVTQQLI            1013
1014 RAAEIRASANLAATKMSECVLGQSKRVDFCGKGYHLMSFPQSAPHGVVFL            1063
1064 HVTYVPAQEKNFTTAPAICHDGKAHFPREGVFVSNGTHWFVTQRNFYEPQ            1113
1114 IITTDNTFVSGNCDVVIGIVNNTVYDPLQPELDSFKEELDKYFKNHTSPD            1163
1164 VDLGDISGINASVVNIQKEIDRLNEVAKNLNESLIDLQELGKYEQYIKWP            1213
1214 WYIWLGFIAGLIAIVMVTIMLCCMTSCCSCLKGCCSCGSCCKFDEDDSEP            1263
1264 VLKGVKLHYT  (SEQ ID NO: 12)
```

FIG. 6B)

```
14   QCVNLTTRTQLPPAYTNSFTRGVYYPDKVFRSSVLHSTQDLFLPFFSNVT              63
64   WFHAIHVSGTNGTKRFDNPVLPFNDGVYFASTEKSNIIRGWIFGTTLDSK             113
114  TQSLLIVNNATNVVIKVCEFQFCNDPFLGVYYHKNNKSWMESEFRVYSSA             163
164  NNCTFEYVSQPFLMDLEGKQGNFKNLREFVFKNIDGYFKIYSKHTPINLV             213
214  RDLPQGFSALEPLVDLPIGINITRFQTLLALHRSYLTPGDSSSGWTAGAA             263
264  AYYVGYLQPRTFLLKYNENGTITDAVDCALDPLSETKCTLKSFTVEKGIY             313
314  QTSNFRVQPTESIVRFPNITNLCPFGEVFNATRFASVYAWNRKRISNCVA             363
364  DYSVLYNSASFSTFKCYGVSPTKLNDLCFTNVYADSFVIRGDEVRQIAPG             413
414  QTGKIADYNYKLPDDFTGCVIAWNSNNLDSKVGGNYNYLYRLFRKSNLKP             463
464  FERDISTEIYQAGSTPCNGVEGFNCYFPLQSYGFQPTNGVGYQPYRVVVL             513
514  SFELLHAPATVCGPKKSTNLVKNKCVNFNFNGLTGTGVLTESNKKFLPFQ             563
564  QFGRDIADTTDAVRDPQTLEILDITPCSFGGVSVITPGTNTSNQVAVLYQ             613
614  DVNCTEVPVAIHADQLTPTWRVYSTGSNVFQTRAGCLIGAEHVNNSYECD             663
664  IPIGAGICASYQTQTNSPRRARSVASQSIIAYTMSLGAENSVAYSNNSIA             713
714  IPTNFTISVTTEILPVSMTKTSVDCTMYICGDSTECSNLLLQYGSFCTQL             763
764  NRALTGIAVEQDKNTQEVFAQVKQIYKTPPIKDFGGFNFSQILPDPSKPS             813
814  KRSFIEDLLFNKVTLADAGFIKQYGDCLGDIAARDLICAQKFNGLTVLPP             863
```

FIGURE 6 cont'd

```
 864  LLTDEMIAQYTSALLAGTITSGWTFGAGAALQIPFAMQMAYRFNGIGVTQ   913
 914  NVLYENQKLIANQFNSAIGKIQDSLSSTASALGKLQDVVNQNAQALNTLV   963
 964  KQLSSNFGAISSVLNDILSRLDPPEAEVQIDRLITGRLQSLQTYVTQQLI  1013
1014  RAAEIRASANLAATKMSECVLGQSKRVDFCGKGYHLMSFPQSAPHGVVFL  1063
1064  HVTYVPAQEKNFTTAPAICHDGKAHFPREGVFVSNGTHWFVTQRNFYEPQ  1113
1114  IITTDNTFVSGNCDVVIGIVNNTVYDPLQPELDSFKEELDKYFKNHTSPD  1163
1164  VDLGDISGINASVVNIQKEIDRLNEVAKNLNESLIDLQELGKYEQYIKWP  1213
1214  WYIWLGFIAGLIAIVMVTIMLCCMTSCCSCLKGCCSCGSCCKFDEDDSEP  1263
1264  VLKGVKLHYT  (SEQ ID NO: 13)                         1273
```

FIG. 6C)

```
  14  QCVNLTTRTQLPPAYTNSFTRGVYYPDKVFRSSVLHSTQDLFLPFFSNVT    63
  64  WFHAIHVSGTNGTKRFDNPVLPFNDGVYFASTEKSNIIRGWIFGTTLDSK   113
 114  TQSLLIVNNATNVVIKVCEFQFCNDPFLGVYYHKNNKSWMESEFRVYSSA   163
 164  NNCTFEYVSQPFLMDLEGKQGNFKNLREFVFKNIDGYFKIYSKHTPINLV   213
 214  RDLPQGFSALEPLVDLPIGINITRFQTLLALHRSYLTPGDSSSGWTAGAA   263
 264  AYYVGYLQPRTFLLKYNENGTITDAVDCALDPLSETKCTLKSFTVEKGIY   313
 314  QTSNFRVQPTESIVRFPNITNLCPFGEVFNATRFASVYAWNRKRISNCVA   363
 364  DYSVLYNSASFSTFKCYGVSPTKLNDLCFTNVYADSFVIRGDEVRQIAPG   413
 414  QTGKIADYNYKLPDDFTGCVIAWNSNNLDSKVGGNYNYRYRLFRKSNLKP   463
 464  FERDISTEIYQAGSTPCNGVEGFNCYFPLQSYGFQPTYGVGYQPYRVVVL   513
 514  SFELLHAPATVCGPKKSTNLVKNKCVNFNFNGLTGTGVLTESNKKFLPFQ   563
 564  QFGRDIADTTDAVRDPQTLEILDITPCSFGGVSVITPGTNTSNQVAVLYQ   613
 614  GVNCTEVPVAIHADQLTPTWRVYSTGSNVFQTRAGCLIGAEHVNNSYECD   663
 664  IPIGAGICASYQTQTNSPRRARSVASQSIIAYTMSLGAENSVAYSNNSIA   713
 714  IPTNFTISVTTEILPVSMTKTSVDCTMYICGDSTECSNLLLQYGSFCTQL   763
 764  NRALTGIAVEQDKNTQEVFAQVKQIYKTPPIKDFGGFNFSQILPDPSKPS   813
 814  KRSFIEDLLFNKVTLADAGFIKQYGDCLGDIAARDLICAQKFNGLTVLPP   863
 864  LLTDEMIAQYTSALLAGTITSGWTFGAGAALQIPFAMQMAYRFNGIGVTQ   913
 914  NVLYENQKLIANQFNSAIGKIQDSLSSTASALGKLQDVVNQNAQALNTLV   963
 964  KQLSSNFGAISSVLNDILSRLDPPEAEVQIDRLITGRLQSLQTYVTQQLI  1013
1014  RAAEIRASANLAATKMSECVLGQSKRVDFCGKGYHLMSFPQSAPHGVVFL  1063
1064  HVTYVPAQEKNFTTAPAICHDGKAHFPREGVFVSNGTHWFVTQRNFYEPQ  1113
1114  IITTDNTFVSGNCDVVIGIVNNTVYDPLQPELDSFKEELDKYFKNHTSPD  1163
1164  VDLGDISGINASVVNIQKEIDRLNEVAKNLNESLIDLQELGKYEQYIKWP  1213
1214  WYIWLGFIAGLIAIVMVTIMLCCMTSCCSCLKGCCSCGSCCKFDEDDSEP  1263
1264  VLKGVKLHYT  (SEQ ID NO: 14)
```

FIGURE 7

```
  1 CACCACCACCACCACCACTGACTCGAGGCTGGAGCCTCGGTGGCCATGCT  50
                   4(e)                    4(a)
 51 TCTTGCCCCTTGGGCCTCCCCCAGCCCTCCTCCCCTTCCTGCACCCGT 100
                              4(a)
101 ACCCCCGGGTCTTTGAGATCTGGTTACCACTAAACCAGCCTCAAGAACAC 150
            4(a)                      4(b)
151 CCGAATGGAGTCTCTAAGCTACATAATACCAACTTACACTTTACAAAATG 200
                              4(b)
201 TTGTCCCCCAAAATGTAGCCATTCGTATCTGCTCCGTTGCCAAAGAAAGT 250
                              4(b)
251 TTCTTCACATTCTAAAAAAAAAAAAAAAAAAAAAAAAAAAAAAAAAAAA 300
            4(b)                      4(c)
301 AAAAAAAAAAAAAAAAAAAAAAAAAAAAAAAAAAAAAAAAAAAAAAAAAA 350
                              4(c)
351 AAAAAAAAAAAAAAAAAAAAAAAAAAAAAAAAAAAAAAAAAAAGGC 396
                      4(c)                    4(d)
```

(SEQ ID NO: 15)

VACCINE FOR USE AGAINST CORONAVIRUS AND VARIANTS THEREOF

FIELD OF THE INVENTION

The present invention generally relates to vaccines, and in particular, to vaccines that are useful against Coronavirus.

SUBMISSION OF SEQUENCE LISTING

The contents of the electronic submission of the text file Sequence Listing, which is named GOW-41411.Sequenc.List.5.19.2022.txt, which was created May 19, 2022 and is 56 KB in size, is incorporated herein by reference in its entirety.

BACKGROUND

A new infectious coronavirus (SARS-CoV-2) was first reported in Wuhan, China in December, 2019 that causes COVID-19. The World Health Organization (WHO) declared COVID-19 a global public health emergency situation on Feb. 5, 2020 after obtaining growing evidence of continuous person-to-person transmission. The virus spread worldwide quickly, and consequently WHO declared it pandemic in March of 2020. As of Dec. 21, 2020, the pandemic has resulted in 1,701,187 deaths among over 42 77,243,764 patients in 220 countries, with a case-fatality rate of 2.20%.

There will be a risk of pandemic as long as there is a COVID-19 epidemic situation in any part of the world unless people are properly vaccinated. Therefore, effective vaccines against SARS-CoV-2 are required to control morbidity and mortality related to COVID-19. Generally, non-replicating viral vectors, inactivated virus, DNA-based and protein-based vaccines have been the major approaches for the development of stable and effective vaccines; although, they have their inherent limitations. Recently, mRNA-based vaccines have become a promising approach because of their opportunity for rapid development, comparative low dose, and better safety profile in terms of no potential risk of infection or insertional mutagenesis, and low capital expenditure (CAPEX).

Several leading vaccines have been developed as well as others which are currently under development against SARS-CoV-2, including vaccines which are mRNA-based. Lipid nanoparticle technology has been developed for effective delivery of single-stranded therapeutics like siRNA, antisense oligo, mRNA etc. The first RNA-LNP therapeutic was approved in 2018 and has set the example for clinical safety of LNP-formulated RNA. Two approved vaccines against SARS-CoV-2 are mRNA vaccines (developed by Pfizer-BioNTech and Moderna Inc.) and they have been successfully used to vaccinate millions of people.

Coronaviruses have genetic proofreading mechanisms, and SARS-CoV-2 sequence diversity is comparatively low; although, natural selection can adopt rare but favorable mutations. Since the outbreak in China, SARS-CoV-2 has gone through numerous mutations. The D614G amino acid change, among these, in the spike protein of Wuhan reference strain is caused by an A-to-G nucleotide substitution at position 23,403 of the relevant nucleotide sequence. Currently, D614G is the most prevalent circulating isotype of SARS-CoV-2 worldwide (more than 95%). The G614 genotype is associated with increased case fatality rate over D614. Scientific findings have demonstrated that the G614 variant is ~10 times more infectious over the D614 genotype. It has also been revealed from in vitro and clinical data that the G614 variant has a distinct phenotype, and there is likely be a huge impact of this mutation on infection, transmission, disease onset, disease prognosis, as well as on vaccine and therapeutic development.

To date, there is no published report regarding D614G-relevant vaccine development. A few studies have shown that antibody generated using D614G variant-target did not show a significant difference between D614 and G614 variants in terms of cellular entry. These studies did not use G614-specific antibody, and applied artificial systems for characterizing relevant functional experiments. Furthermore, it is not known how the G614 variant vaccine will behave on immunization in humans and the impact of the relevant antibody on SARS-CoV-2.

Besides D614G, which is a constant mutation in all published variants, other prevalent mutations in the spike protein include: K417N, K417T, L452R, T478K, E484Q, E484K, N501Y, A570D, H655Y, P681R, P681H etc. Among them L452R, E484K, N501Y, A570D, D614G and P681H are referred to as the Alpha variant (B.1.1.7); K417N, E484K, N501Y and D614G are referred to as the Beta variant (B.1.351, B.1.351.2, B.1.351.3); K417T, E484K, N501Y, D614G and H655Y are referred to as the Gamma variant (P.1, P.1.1, P.1.2); and L452R, T478K, D614G and P681R are referred to as the Delta variant (B.1.617.2, AY.1, AY.2). The Delta variant is the most prevalent variant around the globe. However, there is no reported vaccine candidate that has taken these mutations into consideration.

Therefore, development of a G614 variant-specific vaccine is of prime importance.

SUMMARY

A transgene for use in coronavirus vaccine has now been developed incorporating a spike protein variant-targeted nucleic acid sequence, as well as other immunogen-enhancing aspects.

Thus, in one aspect of the invention, a transgene is provided that encodes:
  i) an RNA polymerase promoter;
  ii) a 5' UTR;
  iii) a secretory sequence;
  iv) a coronavirus spike protein component, wherein the spike protein component incorporates a variant sequence at amino acid position 614 of a native spike protein, and optionally variant sequences at one or both of amino acid positions 452 and 501 of the native spike protein; and
  v) a 3' UTR and poly A sequence.

In another aspect of the invention, a vaccine incorporating a transgene as described above encoding a spike protein variant sequence at amino acid positions 452, 501 and 614 of a native spike protein is provided.

In another aspect of the invention, a method of vaccinating a mammal is provided comprising administering to the mammal a vaccine incorporating a transgene that encodes: i) an RNA polymerase promoter; ii) a 5' UTR; iii) an IgE-based secretory sequence; iv) a coronavirus spike protein component, wherein the spike protein component incorporates a variant sequence at amino acid position 614 of a native spike protein or a position that corresponds with the amino acid position at position 614 of the native spike protein, and optionally variant sequences at one or both of amino acid positions 452 and 501 of the native spike protein, and v) a 3' UTR and poly A sequence.

These and other aspects of the invention are described in the detailed description that follows by reference to the following figures.

BRIEF DESCRIPTION OF THE FIGURES

FIGS. 1A-1H respectively provide: FIG. 1A is a schematic of a transgene depicting L452, N501Y, D614G, K986P, and V987P (as shown in SEQ ID NO: 14) in accordance with an embodiment of the invention, FIGS. 1B-1D are DNA sequencing electropherogram data of L452, N501Y and D614G sequence (as shown in SEQ ID NO: 14) in the target respectively, FIG. 1E is a transient extracellular protein expression in Flp-In CHO and Lenti-X 293T cells where lane 1 is the positive control of Spike S2 ECD-His recombinant protein, lane 2-3 are natural spike extracellular protein containing RYG variant in Flp-In CHO and Lenti-X 293T cells respectively, lane 4-5 are GC-rich codon optimized spike extracellular protein containing RYG variant in Flp-In CHO and Lenti-X 293T cells respectively, and lane 6 is the reference protein ladder, FIG. 1F is a IVT optimization where Lane 4 is the optimized condition, FIG. 1G represents identification of purified capped mRNA by SEC-HPLC, and FIG. 1H represents particle size distribution of mRNA-LNP dose formulation;

FIG. 2A represents an antibody titer analysis from serum of different groups after 14 and 35 days of immunization (n=6), data were 630 compared by Mann-Whitney test, **=p-value <0.0001, *=p-value <0.001, **=p-631 value <0.01; FIG. 2B depicts the ratio of IgG2a and IgG1 in treatment groups, FIG. 2C depicts the ratio of IgG2a+IgG2b and IgG1+IgG3 in treatment groups, FIG. 2D represents serum antibody affinity analysis, and FIG. 2E represents resin pull-down serum antibody affinity analysis.

FIGS. 3A-3M graphically illustrate, respectively, cellular immune response analysis (cellular and secretory cytokine) in control and treatment groups (n=3 for each mentioned otherwise) including: FIG. 3A depicts IFN-gamma expressing cell population percentage at Day 14, treatment n=2; FIG. 3B depicts IL-2 expressing cell population percentage at Day 14, FIG. 3C depicts TNF-α expressing cell population percentage at Day 14, FIG. 3D depicts IL-6 expressing cell population percentage at Day 14, FIG. 3E depicts secretory IFN-gamma concentration at 6 and 18 hours, FIG. 3F depicts secretory IL-2 concentration at 6 and 18 hours, FIG. 3G depicts secretory IL-4 concentration at 6 and 18 hours, FIG. 3H depicts secretory IL-6 concentration at 6 and 18 hours, FIG. 3I depicts CD4+ cell population at Day 91, stimulated with S1 peptide pool, FIG. 3J depicts CD4+ cell population at Day 91, stimulated with S2 peptide pool, FIG. 3K depicts CD8+ cell population at Day 91, stimulated with S1 peptide pool, FIG. 3L depicts CD8+ cell population at Day 91, stimulated with S2 peptide pool, and FIG. 3M depicts CD27+ memory B cell population at Day 91, stimulated with S1 peptide pool (unpaired T-test were performed between control and treatment groups; *=p-value <0.001, =p-643 value <0.01, *=p-value <0.05).

FIGS. 4A-4K graphically illustrate, respectively, the results of in vitro neutralization assays including: FIG. 4A represents an image of Green fluorescence protein (GFP) expression after adeno-based SARS-CoV-2 pseudovirus neutralization assay from 2-4 sample dilution, FIG. 4B depicts the correlation between SARS-CoV-2 antibody from mice sera and intensity of GFP in different experimental groups, FIG. 4C depicts adeno-based SARS-CoV-2 pseudovirus neutralization percentage at different sample dilutions, analyzed by real-time PCR, FIG. 4D depicts HIV-1 based SARS-CoV-2 pseudovirus copy number analysis by real-time PCR, FIG. 4E depicts the inhibition and neutralization assay of the SARS-CoV-2-S pseudo-type virus; all the samples were compared by one-way ANNOVA method, *=p-664 value <0.001, =p-value <0.01, *=p-value <0.05, FIG. 4F depicts fluorescence image of lung section of control group mouse, FIG. 4G depicts trans image of lung section of control group mouse, FIG. 4H depicts overlay image of lung section of control group mouse, FIG. 4I depicts fluorescence image of lung section of treatment group mouse, FIG. 4J depicts trans image of lung section of treatment group mouse, and FIG. 4K depicts overlay image of lung section of treatment group mouse, intentional green color enhancement was done to observe any GFP intensity.

FIGS. 5A-5D illustrate nucleotide sequences of exemplary SARS-CoV-2 spike protein components comprising: FIG. 5A depicts D614G, K986P and V987P mutations (SEQ ID No. 8); FIG. 5B depicts GC-rich and codon optimized synthetic sequence (amino acid position 14-1273) with D614, and K986P and V987P mutations (SEQ ID No. 9); FIG. 5C depicts GC-rich and codon optimized synthetic sequence (amino acid position 14-1273) with D614G, K986P and V987P mutations (SEQ ID No. 10); and FIG. 5D depicts GC-rich and codon optimized synthetic sequence (amino acid position 14-1273) with L452R, N501Y, D614G, K986P and V987P mutations (SEQ ID No. 11);

FIGS. 6A-6C illustrate amino acid sequences of exemplary SARS-CoV-2 spike protein components comprising: FIG. 6A depicts D614G, K986P and V987P mutations (SEQ ID No. 12); FIG. 6B depicts D614, and K986P and V987P mutations (SEQ ID No. 13); and FIG. 6C depicts L452R, N501Y, D614G, K986P and V987P mutations (SEQ ID No. 14); and FIG. 7 illustrates the nucleotide sequence of a 3'-UTR sequence incorporated within a transgene in accordance with an embodiment of the invention, including a spacer sequence at nucleotide positions 1 to 27, modified 3'-UTR of alpha-1-globin at nucleotide positions 28 to 115, modified 3'-UTR of β-globin at positions 116 to 263, a poly A tail followed by a spacer (GGC) (SEQ ID No. 15).

DETAILED DESCRIPTION

Figure 2A:
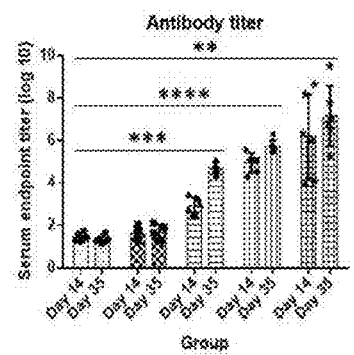
FIGS. 2A-2E graphically illustrate, respectively.
Figure 2B:
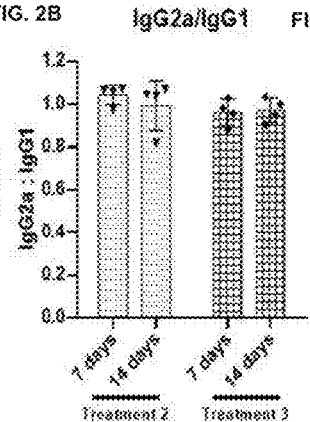
Figure 2C:
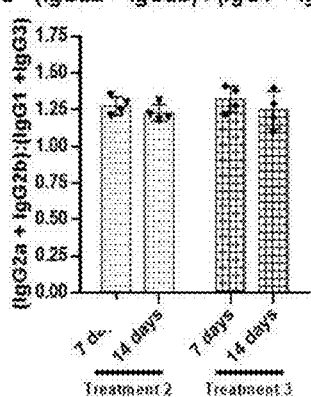
Figure 2D:
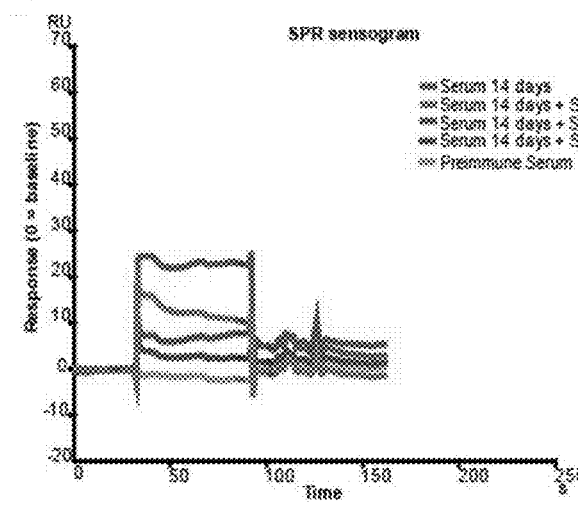
Figure 2E:
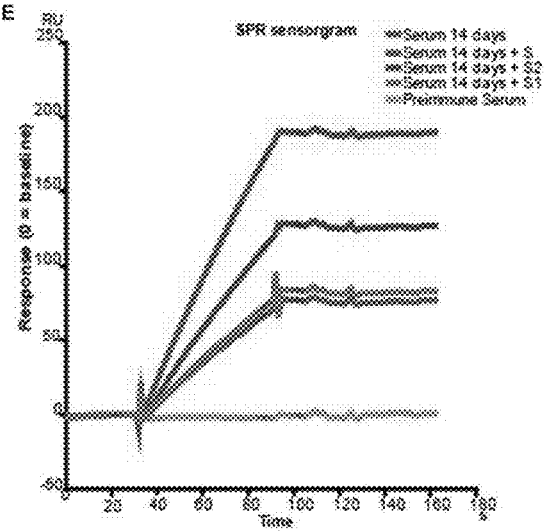

A transgene for use in a coronavirus vaccine is provided. The transgene encodes: i) an RNA polymerase promoter; ii) a 5' UTR; iii) a secretory sequence; iv) a coronavirus spike protein component, wherein the spike protein component incorporates a variant sequence at amino acid position 614 of a native spike protein or a position that corresponds with the amino acid position 614 of the native spike protein, and optionally variant sequences at one or both of amino acid positions 452 and 501 of the native spike protein; and v) a 3' UTR and poly A sequence.

The coronavirus is an enveloped RNA virus with a nucleocapsid of helical symmetry and club-shaped spikes that project from surface. The coronavirus is one of the largest RNA viruses, having a genome that ranges in size from approximately 26 to 32 kilobases. Coronaviruses comprise four genera: Alphacoronavirus, Betacoronavirus, Gammacoronavirus and Deltacoronavirus, and of these, Alphacoronaviruses and Betacoronaviruses infect mammals. Coronaviruses (CoV) include common cold viruses, such as HCoV-229E, HCoV-HKU1, HCoV-NL63, and HCoV-OC43, as well as SARS-CoV. The term "SARS-CoV" refers to a coronavirus that causes severe acute respiratory syndrome. Examples include SARS-CoV1, SARS-CoV2 and MERS-CoV.

SARS-CoV-2 is an enveloped RNA virus of ~30 kb comprising a 5'-UTR, two ORFs which encode 16 nonstructural proteins such as RNA-dependent RNA polymerase, and a region that encodes structural proteins including a spike protein (S), envelope protein (E), membrane protein (M), and nucleocapsid protein (N). In one embodiment, the SARS-CoV-2 has a genome sequence that essentially corresponds with the reference SARS-CoV-2 sequence deposited at Genbank under accession no. MN997409, a 29882 nucleotide sequence in which the region spanning ribonucleotide positions 21563-25384 encodes the spike (S) protein. The coronavirus spike protein includes a signal peptide located at the N-terminus, the S1 subunit, and the S2 subunit; the last two regions are responsible for receptor binding and membrane fusion, respectively. In the S1 subunit, there is an N-terminal domain and a receptor-binding domain (RBD); while the fusion peptide (FP), heptapeptide repeat sequence 1 (HR1), heptapeptide repeat sequence 2 (HR2), transmembrane (TM) domain, and cytoplasm domain comprise the S2 subunit.

SARS-CoV-2 variants have been identified which incorporate an amino acid change at amino acid position 452 of the native spike protein sequence, referred to herein as a "SARS-CoV-2 452 variant". In one embodiment, the amino acid change is represented by L452R, i.e. substitution of leucine (L) in the native strain with arginine (R) in a variant strain, which results from an T-to-G nucleotide substitution at position 22,917 of the native nucleotide sequence. As used herein, these variant coronaviruses are referred to as the "L452R" or "R452" variant.

SARS-CoV-2 variants have been identified which incorporate an amino acid change at amino acid position 501 of the native spike protein sequence, referred to herein as a "SARS-CoV-2 501 variant". In one embodiment, the amino acid change is represented by N501Y, i.e. substitution of asparagine (N) in the native strain with tyrosine (Y) in a variant strain, which results from an A-to-T nucleotide substitution at position 23,063 of the native nucleotide sequence. As used herein, these variant coronaviruses are referred to as the "N501Y" or "Y501" variant.

SARS-CoV-2 variants have been identified which incorporate an amino acid change at amino acid position 614 of the native spike protein sequence, referred to herein as a "SARS-CoV-2 614 variant". In one embodiment, the amino acid change is represented by D614G, i.e. substitution of aspartic acid (D) in the native strain with glycine (G) in a variant strain, which results from an A-to-G nucleotide substitution at position 23,403 of the native nucleotide sequence. As used herein, these variant coronaviruses are referred to as the "D614G" or "G614" variant.

The present transgene is constructed using well-established methods, and may be constructed for use in a nucleic acid-based vaccine, e.g. an mRNA vaccine or DNA vaccine, a subunit vaccine, a non-replicating viral vaccine, an attenuated viral vaccine and an inactivated viral vaccine.

The transgene encodes: i) an RNA polymerase promoter; ii) a 5' UTR; iii) an IgE-based secretory sequence; iv) a coronavirus spike protein component, wherein the spike protein component incorporates a variant at amino acid position 614 of a native spike protein or a position that corresponds with the amino acid position 614 of the native spike protein, and optionally variant sequences at one or both of amino acid positions 452 and 501 of the native spike protein or a position that corresponds with the amino acid at amino acid positions 452 and/or 501; and v) a 3' UTR and poly A sequence.

The transgene incorporates a sequence encoding a promoter. Generally, the transgene will encode a strong promoter that results in high levels of transcription on binding with a selected RNA polymerase. Examples of suitable promoters include promoters recognized by polymerases of the single-subunit DNA-dependent RNA polymerase (ssRNAP) family, such as the T7 promoter, the T3 promoter, the Sp6 promoter, the mitochondrial RNA polymerase (POLRMT) promoter, and the chloroplastic ssRNAP promoter. The nucleotide sequence encoding the T7 promoter (with an GG cap at position 35-36) is: 5'-TAATACGACTCACTATAGG-3' (SEQ ID No: 1). The nucleotide sequence encoding the T3 promoter (with an GG cap at position 35-36) is: 5'-AATTAACCCTCACTAAAGG-3' (SEQ ID No: 2). The nucleotide sequence encoding the Sp6 promoter (with an AG cap at position 35-36) is: 5'ATT-TAGGTGACACTATAG TAG 3' (SEQ ID No: 3).

To facilitate efficient transcription by the promoter, the transgene also incorporates an upstream spacer sequence adjacent to the promoter sequence. The spacer is generally 10-20 nucleotides in length. In one embodiment, the spacer is 17-18 nucleotides in length. Upstream promoter spacer sequences are generally known in the art, and are not particularly restricted with respect to sequence. In one embodiment, the transgene incorporates a promoter spacer sequence that is a random nucleotide sequence. In another embodiment, the promoter spacer sequence is an AT-rich nucleotide sequence, e.g. comprising 40-50% or more adenine (A) and thymine (T) residues. In another embodiment, the promoter spacer has the following nucleotide sequence: GCCTGGCTTATCGAAAT (SEQ ID No: 4).

The transgene incorporates a 5'-UTR sequence that functions to enhance the transcription and translation of the coding region, e.g. for the spike protein component. The 5'-UTR incorporated into the transgene may be the native 5'-UTR for the coding region of the target coronavirus. Native 5'-UTR sequences are generally about 150-200 nucleotides in length. Alternatively, the 5'-UTR may be a synthetic sequence. In one embodiment, the 5'-UTR sequence is:

```
                                       (SEQ ID No: 5)
5'-GAAATAAGAGAGAAAAGAAGAGTAAGAA

GAAATATAAGAGCTAGCGGTACC-3'.
```

The transgene incorporates a nucleotide sequence that encodes a coronavirus spike protein component that targets SARS-CoV-2 452, 501 and 614 variants, such as the L452R, N501Y and D614G coronavirus variants. Thus, the nucleotide sequence of the spike protein component comprises a nucleotide sequence that essentially corresponds with a native spike protein-encoding sequence except that the nucleotides encoding the amino acid at position 614 of the spike protein, and optionally the nucleotides encoding the amino acid at positions 452 and 501 of the native spike protein, encode a variant amino acid, such as glycine (614), tyrosine (452) and arginine (501). Nucleotide sequences encoding exemplary spike protein components, and the amino acid sequences encoded, are illustrated in FIGS. 5A-5D and FIGS. 6A-6C, respectively. As the spike protein is common across Coronaviridae, but the corresponding amino acid in the spike protein of coronaviruses other than the SARS-CoV-2 virus may occur at a position offset from amino acid positions 452, 501 and 614, it is understood herein that such variants are also SARS-CoV variants. The transgene may encode a full-length variant spike protein, or may encode an antigenic fragment thereof that incorporate nucleotides encoding the variant 614 amino acid, an optionally the variant 452 and 501 amino acids. For example, (i) the transgene may encode an N-terminal fragment up to at least amino acid position 614, (ii) the transgene may encode an N-terminal fragment up to at least amino acid position 541, (iii) a C-terminal fragment including the amino acid at position 452, (iv) a C-terminal fragment including the amino acid at position 319, (v) an internal fragment incorporating at least the region R452-G614, and (vi) an internal fragment incorporating at least the region 319-541 of the spike protein. The transgene comprising L452R, N501Y and D614G variations in the spike protein component may be referred to as the 'RYG' spike protein variant.

The transgene may incorporate one or more additional sequence variations to more specifically target known SARS-CoV-2 variants, for example, the transgene may include a sequence that also encodes the amino acid variant, T478K; or the amino acid variant, E484K; or the amino acid variant, E484Q; or the amino acid variant, K986P; or the amino acid variant, V987P or the amino acid variants; or the amino acid variants, K986P and V987P, or any other combination of these variants, or other amino acid variants.

In addition to the spike protein coding sequence, the spike protein component also incorporates a nucleotide sequence that encodes a secretory sequence which is upstream of the coding sequence. The secretory sequence may be the native secretory sequence for the spike protein, or may be a non-native secretory sequence. The secretory sequence is selected based on its efficient cleavage from the spike protein component when translated so as not to compromise the function of the transgene product. Secretory sequences suitable for use include, but are not limited to, the IgE receptor secretory sequence, erythropoietin secretory sequence, growth hormone secretory sequence, granulocyte colony stimulating factor secretory sequence, fibroblast growth factor secretory sequence, vascular endothelial growth factor secretory sequence, and G-protein coupled receptor family secretory sequences. As one of skill in the art will appreciate, the selected secretory sequence may comprise one or more modifications from its native sequence, i.e. one or more modified nucleotides, provided that such modifications do not adversely affect its cleavage from the spike protein component following translation. In one embodiment, the native secretory sequence of the spike protein is replaced with the secretory sequence of the IgE receptor sequence, 5'-MDWTWILFLVAAATRVHS-3' (SEQ ID No: 6), encoded by the nucleotide sequence, atggactggacctggatcctcttcttggtggcagcagccacgcgagtccactcc (SEQ ID No: 7).

The transgene also incorporates a downstream 3' UTR region to facilitate translation and provide stability to the transcript, and may additionally comprise an upstream ribosome-binding site. As one of skill in the art will appreciate, the ribosome binding site is a sequence of nucleotides upstream of the start codon that function to recruit a ribosome to initiate translation. An exemplary ribosome binding site has the sequence, GCCACC. The 3'-UTR region may correspond with the native coronavirus 3'-UTR, or may incorporate one or more modifications from the native sequence which do not adversely impact its function to facilitate translation and to provide transcript stability. For example, the native 3'-UTR may be replaced with the 3'-UTR of another protein. Examples of 3'-UTRs that are suitable for use in the present transgene include, but are not limited to, one or more of the 3'-UTR of alpha-1-globin, beta-globin, c-fos, metallothionein IG, lipoprotein lipase, glutathione peroxidase 4, glutathione peroxidase 3, glutathione peroxidase 2, c-myc, 15-lipoxygenase, and transferrin receptor 2a. In one embodiment, the 3'-UTR of either or both of alpha-1-globin and beta-globin are included in the present transgene. These 3'-UTR sequences may be used in their native form or modified forms, e.g. including one or more nucleotide modifications that do not adversely affect their function. For example, 3'-UTR of α-1-globin may be modified to delete a "T" residue at position 18, and/or the 3'-UTR of β-globin may be modified to replace the 'TAATAA' sequence with 'GTTGCC' to avoid overlap with the poly-A site. The 3'-UTR region also comprises a poly-A sequence having 50-150 A residues, for example, 100 to 140 A residues, or preferably 120-130 A residues. The 3'-UTR may also comprise an upstream and downstream spacer sequence. In one embodiment, the upstream spacer of the 3'-UTR is a 27 nucleotide sequence and the downstream 3'-UTR sequence is 3 nucleotides in length. In another embodiment, the 3'-UTR incorporates the alpha-1-globin and beta-globin 3'-UTR regions, a 130 residue poly A tail, and spacers at its upstream and downstream ends. An exemplary 3'-UTR is shown in FIG. 7.

For use in an mRNA vaccine, the DNA transgene construct is prepared as described, and mRNA is synthesized therefrom by in vitro transcription of the cDNA template, typically plasmid DNA (pDNA), prepared using methods known in the art. Transcription of the cDNA template is conducted using RNA polymerase that corresponds with the promoter incorporated within the transgene, i.e. T7 RNA polymerase when the T7 promoter is incorporated within the transgene, or Sp6 RNA polymerase when the Sp6 promoter is incorporated within the transgene, etc. For stability and efficient translation, the resultant mRNA strand will include a 3' poly(A) tail, as well as 5' and 3' untranslated regions (UTRs) flanking the coding region, as previously described.

The transcript may also be subjected to post-transcriptional processing to optimize the transcript for therapeutic use. For example, the transcript may be modified to include a 5' mRNA cap to provide protection against enzymatic degradation.

The mRNA vaccine is then formulated for administration. In this regard, mRNA may be complexed with agents or adjuvants which prevent degradation, enhance uptake and promote translation. Examples of such adjuvants include, but are not limited to, cationic polypeptides (e.g. protamine), nanoemulsions, carrier peptides, lipid nanoparticles, liposomes, and immune activator proteins (e.g. CD70, CD40L, TLRs). As will be appreciated by one of skill in the art, the vaccine, and any adjuvants, are administered in a suitable carrier, such as saline or other suitable buffer.

In one embodiment, the mRNA vaccine is formulated for administration in lipid nanoparticles. The lipid nanoparticles will generally comprise: an ionizable cationic lipid (whose positive charge binds to the negatively charged mRNA), a PEGylated lipid (for stability), a phospholipid (for structure), and cholesterol (for structure). The ionizable cationic lipid may be any suitable ionizable cationic lipid such as, but are not limited to, C12-200 (1,1'-((2-(4-(2-((2-(bis (2) amino) ethyl) (2-hydroxydodecyl) amino) ethyl)-piperazin-1-yl) ethyl) azanediyl) bis (dodecan-2-ol)); cKK-E12 (3,6-bis (4-(bis (2-hydroxydodecyl)-amino)v butyl) piperazine-2,5-dione); MC3 ([(6Z,9Z,28Z,31Z)-heptatriaconta-6,9,28, 31-tetraen-19-yl]4-(dimethylamino)butanoate); DOTMA (1,2-di-O-octadecenyl-3-trimethylammonium propane); DDAB (N-decyl-N,N-dimethyldecan aminium bromide)N- decyl-N,N-dimethyldecan-1-aminium bromide); DOTAP (1,2-dioleoyloxy (trimethylammonium) propane); DC-cholesterol ([10,13-dimethyl-17-(6-methylheptan-2-yl)-2,3,4,7,8,9,11,12,14,15,16,17-dodecahydro-1H-cyclopenta[a]phenanthren-3-yl] N-[2 (dimethyl amino) ethyl] carbamate; hydrochloride); GL67 ([(3S)-10,13-dimethyl-17-(6-methylheptan-2-yl)-2,3,4,7,8,9,11,12,14,15,16,17-dodecahydro-1H-cyclopenta[a]phenanthren-3-yl] N-(3-aminopropyl)-N-[4-(3-aminopropylamino)butyl] carbamate); and DODMA (N,N-dimethyl-2,3-bis[(Z)-octadec enoxy]propan-1-amine). Phospholipids suitable to provide structure to the lipid nanoparticle include phosphatidylcholines such as distearoylphosphatidylcholine (DSPC) ([(2R)-2,3-di(octadecanoyloxy)propyl] 2-(trimethylazaniumyl)ethyl phosphate), POPC ([(2R)-3-hexadecanoyloxy-2-[(Z)-octadec-9-enoyl] oxypropyl] 2-(trimethylazaniumyl)ethyl phosphate), DMPC ([(2R)-2,3-di(tetradecanoyloxy)propyl] 2-(trimethylazaniumyl)ethyl phosphate), DPPC ([(2R)-2,3-di(hexadecanoyloxy)propyl] 2-(trimethylazaniumyl)ethyl phosphate) and mixtures thereof. Suitable PEGylated lipids for inclusion in the lipid nanoparticle include, but are not limited to, 1,2-dimyristoyl-rac-glycero-3-methoxypolyethylene glycol-2000 (1,2-DMG PEG2000), 1,3-DMG PEG2000, and mixtures thereof. The lipids are combined in suitable molar ratios to provide the required structure and stability. In one embodiment, the nanoparticle includes the lipids, MC3; DSPC; cholesterol; and DMG-PEG2000 in a molar ratio of MC3:DSPC:cholesterol:PEG of 45-55:8-1:35-40:1-2, such as a ratio of 50:10:38.5:1.5.

To prepare the present nanoparticles, the mRNA in a suitable buffer is combined with the lipids at a ratio of about 3:1 to 7:1 to encapsulate the mRNA. The nanoparticles were treated to obtain a stabilized formulation comprising nanoparticles in the range of 40-180 nm, preferably 70-100 nm, 70-90 nm, or 80-90 nm. For example, the nanoparticles were dialyzed, or buffer exchanged using tangential flow filtration (TFF), to achieve stabilized nanoparticles. Stabilization of the nanoparticles is achieved by a selected treatment for at least about 5 minutes to 24 hours using suitable reagents, including HEPES (2-[4-(2-hydroxyethyl)piperazin-1-yl] ethanesulfonic acid), acetate buffer, phosphate buffered saline (PBS) and Tris (trisaminomethane)-HCL. For example, such as 1 to 100 mM HEPES (pH range: 6.0 to 8.0), 1 to 100 mM Acetate (pH range: 4.0 to 7.5), 1× to 10×PBS (pH range: 6.0 to 8.0) and 1 to 50 mM Tris-HCl (pH range: 6.0 to 8.0), and combinations thereof may be used. The preferable combinations are: 1 to 100 mM HEPES (pH range: 6.0 to 8.0) and 1 to 100 mM Acetate (pH range: 4.0 to 7.5), 1× to 10×PBS (pH range: 6.0 to 8.0) and 1 to 100 mM Acetate (pH range: 4.0 to 7.5), 1 to 50 mM Tris-HCl (pH range: 6.0 to 8.0) and 1 to 100 mM Acetate (pH range: 4.0 to 7.5), 1 to 100 mM HEPES (pH range: 6.0 to 8.0) and 1× to 10×PBS (pH range: 6.0 to 8.0), 1 to 100 mM HEPES (pH range: 6.0 to 8.0) and 1 to 50 mM Tris-HCl (pH range: 6.0 to 8.0), 1 to 100 mM HEPES (pH range: 6.0 to 8.0) and 1 to 100 mM Acetate (pH range: 4.0 to 7.5) with 1× to 10×PBS (pH range: 6.0 to 8.0), 1 to 100 mM HEPES (pH range: 6.0 to 8.0) and 40 to 60 mM Acetate (pH range: 4.0 to 7.5) and 10 to 40 mM Tris-HCl (pH range: 6.0 to 8.0) for at least 5 minutes to 24 hours. More preferably, 40 to 60 mM HEPES and 40 to 60 mM acetate (pH range 6.3 to 7.0), 1x PBS and 40 to 60 mM Acetate (pH range: 6.0 to 7.2), 10 to 40 mM Tris-HCl and 40 to 60 mM Acetate (pH range: 6.0 to 7.5), 40 to 60 mM HEPES and 1×PBS (pH range: 6.0 to 8.0), 40 to 60 mM HEPES and 10 to 40 mM Tris-HCl (pH range: 6.5 to 7.5), 40 to 60 mM HEPES and 40 to 60 mM Acetate and 1×PBS (pH range: 6.5 to 7.0), 40 to 60 mM HEPES and 40 to 60 mM Acetate and 10 to 40 mM Tris-HCl (pH range: 6.8 to 7.5), for at least 5 minutes to 4 hours.

For clarity, the term "acetate buffer" as used herein refers to sodium acetate, potassium acetate, calcium acetate, magnesium acetate, lithium acetate, barium acetate, cesium acetate, iron acetate, aluminium acetate, zinc acetate, coper acetate, ammonium acetate, triethyl ammonium acetate, diethyl ammonium acetate and other suitable acetate salts of inorganic and organic cations/bases and combinations thereof.

Following stabilization, the final nanoparticle product is combined with a suitable solution for administration, e.g. an aqueous solution such as a saline, buffered saline or Tris or mixtures thereof, adjusted to a pH of 7.2+/−0.2. Preferably, the solution comprises sodium chloride (pH range: 7.2+/−0.2), PBS (pH range: 7.2+/−0.2), and Tris-HCl (pH range: 7.2+/−0.2). The nanoparticle solution may additionally comprise stabilizing agents, such as carbohydrates, glycerol, vitamins, antioxidants, anti-reducing agents, and anti-hydrolyzing agents, to maintain the desired particle size during storage. Exemplary stabilizing agents include sucrose, trehalose, mannitol, PEG, propylene glycol, sorbitol, L-arginine, vitamin-A, vitamin-B, vitamin-C, vitamin-E, iron, aluminium, zinc, calcium, magnesium, sodium, potassium, glycerol and combinations thereof, in amounts of 3-20% by wt.

The DNA transgene construct is then generally adapted for administration. The transgene construct may be formulated for administration as a linear molecule, covalently-closed linear construct or mini-circle. Alternatively, the transgene construct may be incorporated into a vector such as a plasmid or cosmid using techniques well-known in the art and then formulated for administration. The resulting DNA vaccine is formulated for administration. The vaccine may be incorporated within a delivery system adapted to enhance immunogenicity of the vaccine, for example, biodegradable polymeric microparticles (e.g. chitosan, polylacticecoglycolides, polyethyleneimine, amine-functionalized polymethacrylates, cationic poly(β-amino esters), poloxamers and polyvinylpyrrolidone polymers) or liposomes. Additional delivery systems may also be used such calcium phosphate, calcium apatite, or calcium hydroxy apatite. The vaccine may also be combined with an adjuvant to enhance immunogenicity, e.g. inorganic compounds such as aluminum-containing compounds and squalene, oils such as paraffin, bacterial products such as toxoids, plant saponins, cytokines such as IL-1, IL-2 or IL-12, a cytosine phosphoguanine (CpG) motif-containing adjuvant, or an adjuvant combination such as Freund's adjuvant.

Viral-vectored vaccines may also be utilized to administer the present transgene construct, including both DNA viral vectors and RNA viral vectors. DNA viral vector vaccines are adapted to expressibly incorporate the present DNA transgene construct, e.g. under the control of a viral promoter. Examples of suitable DNA viruses for use as vaccines include, but are not limited to, poxviruses such as vaccinia virus and modified vaccinia virus, adenoviruses, adeno-associated viruses, herpes simplex virus and cytomegalovirus, and including various serotypes thereof, both replication-competent and replication-deficient. RNA viral vector vaccines may also be adapted to expressibly incorporate an appropriate transcript of the present transgene construct, e.g. positive or negative strand. Examples of suitable RNA viruses for use as a vaccine to deliver the transgene include, but are not limited to, vesicular stomatitis viruses, retroviruses such as MoMLV, lentiviruses, Sendai viruses, measles-derived vaccines, Newcastle disease virus, alphaviruses such as Semliki Forest virus, flaviviruses, or an RNA replicon based on an RNA virus (i.e. derived from alphavirus, flavivirus, etc).

The present vaccine is used in a method of vaccinating a mammal against infection by a coronavirus. The vaccine is administered to the mammal in a therapeutically effective amount, i.e. an amount sufficient to generate in the mammal an immune response. The term "mammal" is used herein to refer to both human and non-human mammals. As one of skill in the art will appreciate, the amount required to generate an immune response will vary with a number of factors, including, for example, the particular transgene/antigens in the vaccine, the vector used to deliver the vaccine, and the mammal to be treated, e.g. species, age, size, etc. The dosage may also vary based on the form of the vaccine, i.e. DNA vaccine vs. mRNA vaccine, as well as the formulated form of the vaccine. In this regard, suitable dosages may be determined using appropriate well-established means. It is expected that a dosage of to 300 μg, for example 10-100 μg, of the mRNA formulated in lipid nanoparticles will generate a suitable immune response in humans.

The present vaccine is administered to a mammal to prevent a coronavirus infection in any one of several administrable routes including, but not limited to, parenteral administration such as intravenously or intramuscularly, intranasally or by inhalation. For nucleic acid-based vaccines, other techniques such as administration by electroporation or using gene gun technology may be utilized.

The vaccine may be administered using a prime/boost protocol. In this regard, the prime and boosting vaccines, which may be the same or different vaccine type (e.g., both the prime and boosting vaccine may be a nucleic acid-based vaccine, or both may be a viral vectored vaccine, or the prime vaccine may be nucleic acid-based and the boosting vaccine may be a viral vector, or vice versa) are administered such that the boost is administered once the immune response to the prime dose has reached a suitable level, e.g., a period of time of about 1-26 weeks following the prime dose. The prime and boosting doses may be administered by the same or different administrable routes.

In an embodiment, the present vaccine is formulated as an mRNA vaccine in a lipid nanoparticle and is administered in two doses, i.e., administration of a prime (first dose) followed by administration of a boost ($2^{nd}$ dose), within about 4-12 weeks, so as to generate a sufficient immune response.

In another embodiment, the present vaccine is formulated as an mRNA vaccine in a lipid nanoparticle and is administered using a single administration, i.e., administration of a boost is not required to generate a sufficient immune response.

The present vaccine advantageously results in a vaccine that generates a strong immune response and neutralization efficacy against SARS-CoV-2 variants, including the Alpha, Beta, Gamma and Delta variants. To date, a vaccine targeting such SARS-CoV-2 variants has not been developed. The present vaccine is based on a transgene designed to yield high levels of mRNA vaccine, with enhanced stability, processability and little or no toxicity. In addition, in an embodiment, the mRNA vaccine may be provided as a lipid nanoparticle vaccine which provides efficient mRNA release on administration and uptake by antigen-processing cells. The present vaccine is confirmed to elicit neutralizing antibodies and a beneficial balanced cellular response (e.g. Th1:Th2 is approximately equal, i.e. about 1:1).

Embodiments of the invention are described by reference to the following specific Example which are not to be construed as limiting.

Example

The following work describes the development of an mRNA vaccine in accordance with an embodiment of the present invention.

Methods

Target gene and vector cloning—The target DNA was identified using data mining and analysis using bioinformatics. The target DNA was amplified from a patient sample, sequence confirmed, modified to achieve the desired design architecture such that it harbors a suitable 5' UTR, ORF to express the S protein with R452, Y501, G614 and double proline (2P) mutations (K986P and V987P) with an IgE-90 secretory signal sequence, a special 3' UTR constructed with modified alpha and beta globin in tandem, and finally a 130 residue-long poly-A tail. For overexpression of S protein, a GC-rich codon optimized S gene was prepared using in-house developed using a polymerase chain assembly method. After assembly of the S gene, it was replaced with the above-mentioned construct.

Target selection—As of March 2020, there were 170 surface glycoproteins (partial and complete sequence) out of 1661 SARS-COV-2 proteins posted on NCBI Virus database. A comparative sequence alignment using Clustal Omega (ebi.ac.uk/Tools/msa/clustalo/) showed differences in several regions, notably in position 614 (D>G). A total of 15 glycine containing surface glycoproteins were found. A consensus sequence from multiple sequence alignment was identified using EMBOSS Cons (ebi.ac.uk/Tools/msa/emboss_cons/) and selected as a primary target sequence for vaccine development. Hydrophilicity/hydrophobicity plot analysis was performed using GENETYX Ver8.2.0, protein 3D modeling using Phyre2 and visualized using UCSF Chimera 1.11.2rc. The R452, Y501, D614G and double proline (2P) mutations (K986P and V987P) were incorporated into the target sequence.

Target amplification—Nasopharyngeal and oropharyngeal swab sample were collected from a COVID-19 positive male patient. Virus heat inactivation at 56° C. for 30 minutes and total RNA including virus RNA extraction was performed using TRIzol™ Plus RNA Purification Kit (ThermoFisher, USA). cDNA synthesis was performed using GoScript™ Reverse Transcription System (Promega, USA). S-gene (Surface glycoprotein) was amplified using 3 different sets of primers and Platinum™ SuperFi™ DNA Polymerase (ThermoFisher, USA). Amplified S-gene and polymerase chain reaction (PCR) engineered pET31b(+) (Novagen, Germany) bacterial expression vector were amplified, excised and extracted from agarose gel using GeneJET Gel Extraction and DNA Cleanup Micro Kit (ThermoFisher, USA), and assembled together using NEBuilder® HiFi DNA Assembly Master Mix (NEB, USA). Sub-cloning was performed into DH5α chemical competent cells, miniprep purification was using PureLink™ Quick Plasmid Miniprep Kit (ThermoFisher, USA). S-gene integration check into vector was performed via restriction digestion using XbaI (ThermoFisher, USA) and EcoRI (ThermoFisher, USA), and PCR using primers. DNA sequencing was performed to confirm the complete open reading frame (ORF) compatibility of target S-gene. Finally, sequence confirmed rDNA (rDNA ID: p20004) was further amplified and purified using PureLink™ HiPure Plasmid Midiprep Kit (ThermoFisher, USA), sequenced, and stored for future purposes. Also, sequence confirmed S-gene was submitted to NCBI (GenBank accession number MT676411.1), where we identified and noted D614G mutation. Supplier's manual with minor modifications were followed for all the methods.

Target modification—An immunoglobulin (Ig) heavy chain (HC) 19 amino acid signal peptide (H1) was assembled, and amplified along with homology arm for incorporating into rDNA p20004, replacing native 13 amino acid leader sequence. Assembled signal peptide was amplified with homology arm and rDNA p20004 was engineered via PCR. New rDNA p20006 was prepared by incorporating signal peptide and engineered p20004 rDNA, using above explained method as p20004 rDNA preparation. S-gene was amplified from rDNA p20006. This gene and pcDNA™5/FRT Mammalian Expression Vector (ThermoFisher, USA) were digested using Acc65I (ThermoFisher, USA) and XhoI (ThermoFisher, USA) and visualized via agarose gel electrophoresis. The desired bands from the gel were excised and purified using GeneJET Gel Extraction and DNA Cleanup Micro Kit and ligated using T4 DNA Ligase (ThermoFisher, USA). After ligation, sub-cloning into DH5α chemical competent cells, plasmid miniprep purification, insert checking, DNA sequencing, plasmid midiprep purification, DNA sequencing and storage (rDNA ID: p20010) were performed. Amino acid mutations at position 452 (L452R), 501 (N501Y), and 2P (double Proline) amino acid mutations at position 986 (K986P) and 987 (V987P) were also performed via site directed mutagenesis. DNA sequencing was performed to confirm desired mutations (rDNA ID: p20015). Finally, a T7 promoter sequence, a synthetic 5'-UTR, an IgE signal peptide replacing native 13 amino acids signal peptide from S-gene, a 3'-UTR (modified alpha globin and modified beta globin), and a 130 bp synthetic poly A-tail (pA-tail) were added. A restriction endonuclease (Sfo I) sequence before T7 promoter sequence and after pA were added for cutting out desired size of DNA for in vitro mRNA synthesis (rDNA ID: p20020.2). A GC-rich codon optimized S gene was assembled via in-house developed polymerase chain assembly method for the purpose of overexpression of S protein. After assembly and amplification of S gene, it was replaced with natural S gene from the rDNA p20020.2 and generated a new rDNA p21004. Final rDNA ID was p20020, p20020.3, p20020.2, p21005, p21006, p21004, p21009 and rDNA construction was performed as mentioned before for p20004 and p20006. Supplier's manual with minor modifications were followed for all the methods.

Sequencing—DNA sequencing was performed as according to supplier's protocol for the final construct p20020, 20020.3, p20020.2, p21005, p21006, p21004, p21009 and other constructs e.g., p20004, p20006, p20010, p20013, p20013.1, p20015, p20026, p20026.1, p20030, p20030.1, p20031, p20031.1, p21010, p21011, p21012, etc. using 3500 Genetic Analyzer (ThermoFisher, USA). DNA sequencing data clearly confirmed the presence of the target sequences and modifications. BigDye® Terminator v1.1 Cycle Sequencing Kits (ThermoFisher, USA) and POP-6 polymer (ThermoFisher, USA) chemistry was used for DNA sequencing reaction.

mRNA production—The in vitro transcription (IVT) of mRNA was performed in the presence with 3'-O-Me-m7G (5)ppp(5')G RNA Cap Structure Analog and S-adenosylmethionine (NEB, USA) using MEGAscript™ T7 Transcription Kit (ThermoFisher, USA), and Ribonucleotide Solution Set (NEB, USA). IVT mRNA synthesis reaction was optimized into 4 steps (step 1: synthesis time factor, step 2: rNTPs concentration, step 3: RNase inhibitor and pyrophosphatase effect, and step 4: temperature dependency); final concentration of ribonucleotides was as follows: ATP and UTP—13.13 mM, and GTP and CTP—9.38 mM. The reaction was run for 2 hours at 37° C. followed by a DNase treatment at 37° C. for 15 minutes and dephosphorylation using Antarctic Phosphatase (NEB, USA) according to supplier's manual. IVT capped mRNA was purified using phenol:chloroform:isoamyl alcohol, and purified using MEGAclear™ Transcription Clean-Up Kit (ThermoFisher, USA).

mRNA identification—Capped mRNA, purified mRNA, formulated lipid nanoparticles (LNPs) and formulated LNPs, treated with RNase samples, were analyzed by size exclusion chromatography (SEC). SEC was performed in Ultimate 3000 (ThermoFisher, USA) system using 10 mM Disodium hydrogen phosphate (Wako, Japan), 10 mM Sodium dihydrogen phosphate (Wako, Japan), 100 mM Sodium chloride (Merck, Germany), pH 6.6 as mobile phase. Biobasic SEC-300 (300×7.8 mm, particle size; 5 μm, ThermoFisher, USA) column was used with 1.0 mL/minute flow rate, 260 nm wavelength, 10 μL sample injection volume for 20 minutes.

Formulation of mRNA—Purified mRNAs were first diluted with sodium acetate buffer to the desired concentration. The lipid molecules were dissolved in ethanol and mixed well. Lipids (MC3:DSPC:cholesterol:DMG-PEG2000) were combined in a molar ratio of 50:10:38.5: 1.5. Then, sodium acetate buffer containing mRNA and the lipid samples were mixed at a ratio of 3:1 to 7:1 and passed through the liposome extruder (Genizer, USA) or were made with another suitable liposome technology, for example, T-mixture, Y-mixture, Herringbone mixture, diffusion film mixture etc. to encapsulate the mRNA. The size distribution was checked after encapsulation of mRNA into nanoparticles. Then, the samples were stabilized through dialysis or other suitable technologies for example, TFF or dilution against 40 to 60 mM HEPES and 40 to 60 mM sodium acetate (pH range 6.5 to 6.9) for 3.0 hours. After completion of stabilization, samples were formulated through dialysis against 1×PBS (pH range: 7.2+/−0.2) or 20 mM Tris-HCl (pH range: 7.2+/−0.2). To maintain the desired LNP size during storage, 7 to 10% by wt sucrose was added. The size distribution was checked by Zetasizer Nano ZSP (Malvern Panalytical, UK). LNP samples were analyzed for size distribution in respective buffers. The formulated sample (referred to as GBPD060) was concentrated using Ultra centrifugal filters or TFF membrane and passed through 0.22 micron filter, and stored at 5±3° C., −30±5° C., −80±5° C. The formulation was confirmed by quality control tests for particle size distribution, encapsulation efficiency, endotoxin limit and sterility.

Animal management and vaccination—The study procedures were performed according to local and international regulation. A total of 50 BALB/c Swiss albino mice (male and female) 6-8 weeks old were selected and isolated 5 days before immunization. After careful observation and conditioning, suitable numbers of mice were selected. The temperature in the experimental animal room was 26° C. (±2° C.) and the relative humidity was 60±5%. The room was HVAC controlled ISO class 7 room with 70% fresh air intake and full exhaust. The mice were individually housed in cages with proper water and feed, and kept under 12 hours of day-night cycle. O30 mice were separated into 5 different groups consisting of 6 mice (3 males and 3 females) in each group. GBPD060 formulations and vehicle were administered intramuscularly (IM) in the quadriceps for treatment and placebo, respectively. Each mouse of group 1, 2 and 3 was immunized with sterile 0.1 µg/50 µL, 1 µg/50 µL, 10 µg/50 µL of GBPD060, respectively. Second dose was administered 21 days later. The sample sizes were determined by the resource equation method.

Local tolerance—Local tolerance was confirmed by clinical signs, and macroscopic and histopathology evaluations of injection sites in animals. Euthanasia and evaluation of lesions was performed in one representative mouse from placebo and control group and 3 from the treatment group at 132 hours post treatment. The inner thigh muscle of injected site of each mouse was excised and placed in 10% neutral buffered formalin until adequately fixed. After trimming, processing and paraffin embedding, the sections (6 µm) are HE stained and observed for erythema and edema under microscope.

Immunogenicity—Approximately 200 µL blood was collected from facial vein and centrifuged at 1500×g for 138 serum isolation (10 minutes at 4° C.). All serum was aliquoted, frozen immediately and stored at −80° C. until analysis. The reactivity of the sera from each group of mice immunized with GBPD060 was measured against SARS-CoV-2 S antigen (SinoBiologicals, China). The serum IgG binding endpoint titers (EPTs) were measured in mice immunized with GBPD060. EPTs were observed in the sera of mice at day 7 and day 14 after immunization with a single dose of GBPD060.

Toxicity—Whole blood (~50 µL) from each mouse was collected in 2% EDTA at 3 days pre-immunization and 14 days post-immunization. Complete blood count (CBC) analysis was measured using an auto hematology analyzer BK-6190-Vet (Biobase, China). Samples were used for blood-chemistry analysis viz., alanine transferase (ALT), aspartate transaminase (AST) and blood urea nitrogen (BUN) using semi-automatic chemistry analyzer (Biobase, China).

Pseudovirus preparation and in vitro neutralization—Adenovirus and retrovirus-based pseudovirus were prepared for SARS-CoV-2 in vitro and in vivo neutralization assay. Pseudotyped-SARS-CoV-2 adenovirus was prepared expressing the SARS-CoV-2 surface glycoprotein gene (S gene) on the virus. S gene of SARS-CoV-2 was cloned into pAADV-B02 vector (Genemedi, China) that also contains a GFP gene downstream of the gene of interest. Site directed mutagenesis was performed to incorporate Q498T and P499Y mutations in the S-gene for the purpose of homotypic pseudovirus preparation. After construction, SARS-CoV-2 S gene containing rDNA and adenovirus backbone plasmid pAADV-C01 (Genemedi, China) were co-transfected into HEK293-based adapted viral production cell (VPC) (ThermoFisher, USA). VPCs were seeded in a 6-well TC-treated plate (Nest, China) at a concentration of $6\times10^5$ cells/well and cultured overnight. Co-transfection were performed using Lipofectamine 3000 (ThermoFisher, USA) reagent according to manufacturer's protocol. Next day 1.25% low melting agarose in DMEM media was spread on the well and incubated until plaques were formed. After formation of plaques, multiple plaques were collected in DMEM media and titers were measured for plaque selection. Then selected plaque was added on the fresh VPC. After few days, cells and supernatant were collected and repeated freeze-thawing was performed for collection of viruses (P1 pseudovirus). These processes were repeated and P4 pseudoviruses were collected; concentration and purification were performed by ultracentrifugation and sucrose gradient. After titer determination, pseudoviruses were stored at −86° C. (ThermoFisher, USA).

Another pseudotyped SARS-CoV-2 retrovirus was prepared as follows. S gene was cloned into pMSCV_Neo vector (TakaRa Bio, USA). After preparation of S gene-expressing plasmid, co-transfection was performed on VPC. pMD2G and pSPAX2 (Genemedi, China) packaging plasmid were used for retro-based pseudovirus preparation. $9\times10^6$ cells were seeded in a 75 cm$^2$ TC-treated flask and cultured overnight. Co-transfection was performed using Lipofectamine 3000 reagent. Media was replaced with complete DMEM after 6 hours. Media was collected after 48 hours and stored at 4° C. 12 mL media was added into the flask, collected the next day and pooled with previously stored media. Then concentration and purification were performed by ultracentrifugation. Pseudoviruses were stored at −86° C. (ThermoFisher, USA) after titer determination.

ACE2-overexpressing HEK293 cells (Innoprot, Spain) were seeded in two 96-well TC-treated plate at a concentration of $2.2\times10^4$ cells/well and incubated overnight. One plate was used for adeno-based pseudovirus and the other plate for retro-based pseudovirus, respectively. Two separate plates were used for serum preparation. Different rows of the plate were used for different groups, such as A1-A10 for treatment group, B1-B10 for placebo, C1-C10, D1-D10 E1-E10 and F1-F10 for control, CR3022, commercial anti spike and only cell group (negative control). Sera from different mice of the same group were collected and pooled for neutralization assay. 10 µL sera from vaccinated mice was added in 90 µL complete DMEM media, and were serially 2-fold diluted up-to 9 times. $1.2\times10^5$ pseudovirus in 50 µL was added into different wells that contained serially diluted serum and mixed properly. The SARS-CoV-2 pseudovirus and serum mixture was incubated for 1.5 hour at 37° C. Then, 100 µL of pseudovirus and serum mixture was transferred on pre seeded cells. 5 µg/mL poly L-lysine (Wako, Japan) was added into each well for enhancing the transduction. Then, incubation was performed at 37° C. for 48 hours and GFP-fluorescence were measured using Varioskan LUX (ThermoFisher, USA). Number of virus particle inside the cells were determined by qPCR (QuantStudio 12K Flex, ThermoFisher, USA). For retro-based neutralization assay, qPCR was used to analyze the copy number of S gene in cell. Genomic DNA was extracted by MagMAX Express-96 Standard (ThermoFisher, USA) using Magmax DNA multi-sample ultra-kit. (ThermoFisher, USA) and used for determination of S gene copy number by qPCR.

In vivo neutralization—18 albino male mice 6-8 weeks of age were selected and divided into 6 groups, 1 control and 5 treatment, comprising 3 male mice in each group. The control group mice were immunized intramuscularly with 50 µL of placebo and treatment group mice were immunized with 1 µg/50 µL of GBPD060 vaccine. GFP pseudo-typed homotypic SARS-CoV-2 adenovirus were sprayed in the nasopharynx on 21-day post immunization. Nasopharynx and lung aspirate samples from mice were collected and analyzed for viral copy number using qPCR at indicated time point. Animals were sacrificed and lung sections were performed and microscopic slides were prepared for fluorescence imaging (GFP) to detect viral load.

Antibody analysis by ELISA—Serum from the mice of different groups were analyzed by standard enzyme-linked immunosorbent assay (ELISA) to determine antibody titers. ELISA plate (Corning, USA) was coated with 1 µg/mL SARS-CoV-2 Spike S1+S2 ECD-His recombinant protein (Sino Biological, China) in Dulbecco's phosphate-buffered saline (DPBS) (ThermoFisher, USA) for 2 hours at room temperature. Plates were washed three times with DPBS+ 0.05% Tween 20 (Scharlau, Spain) and then blocked with PBS+1% BSA (ThermoFisher, USA)+0.050% Tween-20 for 2 hours at 37° C. The plates were washed 3 times then incubated with sera and SARS-CoV-2 Spike antibody (Sino Biological, China) for 2 hours at 37° C. After washing 3 times, the plates were then incubated with HRP conjugated Goat anti-Mouse IgG (H+L) secondary antibody, (ThermoFisher, USA) for 50 minutes at room temperature. Final washing was done 3 times and then the plates were developed for colorimetric detection reaction with Pierce TMB substrate (ThermoFisher, USA) for 10 minutes. The reaction was stopped with 1N hydrochloric acid (HCl) and signals were measured at 450 nm wavelength within 30 minutes. For isotype analysis, Pierce Rapid ELISA Mouse mAb Isotyping kit (ThermoFisher, USA) was used. Serum samples from 4 subjects of treatment 2 and 3 were analyzed. All the steps were followed as per supplier's instructions.

Antibody binding affinity—The BIAcore T200 equipment (GE Healthcare, USA) and Amine coupling kit (GE Healthcare, USA) were used for immobilization of SARS-CoV-2 Spike S1+S2 ECD-His recombinant protein (Sino Biological, China) in Series S Sensor Chips CM5 (GE Healthcare, USA). First, the flow cell surface of Series S Sensor Chips CM5 was activated by injecting a mixture of EDC/NHS (1:1) for 7 minutes. Then 70 μL of 50 μg/mL S1+S2 protein was prepared in sodium acetate at pH 5.0 and injected over the activated surface at 10 μL/min flow rate. Residual NHS-esters were deactivated by a 70 μL injection of 1 M ethanolamine, pH 8.5. The immobilization procedure was performed by using running buffer HBS-EP, pH 7.4 (GE Healthcare, USA). Sera at 14-day post immunization were used for the experiment; 5 samples, each containing either 1 μL sera or MabSelect resin- (GE Healthcare, USA) pulldown sera (IgG) were analyzed using surface plasmon resonance (SPR) to analyze the binding affinity of the antibody pool. Samples (1 μL) were pretreated with 5 μL of either buffer or SARS-CoV-2 S or SARS-CoV-2 S1 or SARS-CoV-2 S2 protein (500 μg/mL) at 25° C. for 15 minutes. All samples were diluted in 1×HBS-EP (pH, 7.4) running buffer. Samples were applied through the active flow cell surface of CM5 chip for binding analysis. Glycine-HCl of pH 2.5 was used for regeneration of the chip.

SARS-CoV-2 surface glycoprotein peptide pool generation and mapping—40 μg of SARS-CoV-2 Spike S1+S2 (S) ECD His recombinant protein (Sino Biological, China), S2 ECD-His Recombinant Protein (Sino Biological, China), and RBD(S1)-His Recombinant Protein (Sino Biological, China) were diluted in 50 mM ammonium bicarbonate (Wako Pure Chemicals Industries Ltd., Japan), pH 8 containing 8 M urea (ThermoFisher Scientific, USA). 500 mM DTT (ThermoFisher Scientific, USA) was added to the solution to a final concentration of 20 mM (1:25 dilution) mixed briefly, and incubated at 60° C. for 1 hour. For alkylation, 1 M IAA (Sigma-Aldrich, USA) was added to the reduced protein sample to a final concentration of 40 mM (1:25 dilution), and the reaction mixture was incubated for 30 minutes protected from light. The reaction was stopped by adding 500 mM DTT solution to a final concentration of 10 mM (1:50 dilution). Enzymes (ThermoFisher Scientific, USA) were added to the sample solution to a final trypsin to protein ratio of 1:23 (w/w). Samples were incubated at 37° C. for 16-24 hours. Reaction was stopped by adding formic acid up-to pH 2.0. C18 spin column (ThermoFisher Scientific, USA) was prepared as per manufacturer's instruction to purify the peptide-pool. Columns were activated by adding 200 μL 50% acetonitrile (Wako Pure Chemicals Industries Ltd., Japan), and equilibrated using 200 μL 0.5% formic acid (Wako Pure Chemicals Industries Ltd., Japan) in 5% acetonitrile (Wako Pure Chemicals Industries Ltd., Japan). Samples were applied to the column and eluted using 20 μL 70% acetonitrile. Samples were dried under low temperature and vacuum and processed for experiments.

SARS-CoV-2 S-ECD His recombinant protein (Sino Biological, China), S2-ECD-His Recombinant Protein (Sino Biological, China), and RBD(S1)-His recombinant proteins (Sino Biological, China) were digested with Serine Protease (MS grade, Pierce, ThermoFisher, USA) and purified according to the supplier's instructions (supplementary method). 1 μg of digested peptides were loaded into mass spectrometry system (Q Exactive Hybrid Quadrupole-Orbitrap MS, ThermoFisher Scientific, USA). For separation of peptides Hypersil gold C18 (100×2.1 mm; particle size: 1.9 μm, ThermoFisher, USA) column was used. Column oven temperature was set at 40° C. and eluted in 95— 60% mobile phase A (0.1% formic acid in water) and 5-40% mobile phase B (0.1% formic acid in acetonitrile) gradient with 0.300 mL/min flow rate for 65 minutes. Peptide elution were checked by UV absorbance at 214 nm. For peptide identification, data dependent mass spectrometry was performed where full-MS scan range was 350 m/z to 2200 m/z, resolution was 70000, AGC target was 3E6, maximum IT was 100 milliseconds (ms). Data dependent mass spectrometry resolution was 17500, AGC target was 1E5 and maximum IT was 100 ms. Data analysis was performed in BioPharma Finder (ThermoFisher, USA) using variable parameters to get confident data, and then data were combined in one map to visualize complete fragmentation.

Mouse splenocyte isolation, peptide stimulation and flow cytometric analysis of Tcell populations—Harvested spleen was taken in RPMI and mashed within the petri dish. Cells were washed out from slides using micropipette. A 10 ml pipette was used to draw the solution up and down, each time closing the end of the pipette against the bottom of the petri dish to forcefully expel the contents and break up the pieces. Cell suspension was passed through a sterile 40 μm mesh strainer. Centrifugation was performed for 10 minutes at 250×g, at 4° C. Supernatants were discarded and cells were re-suspended in 10 mL PBS. Samples were subjected for Ficoll-Paque PLUS processing. Centrifugation was performed for 30 minutes at 400×g at 20° C. Two thirds of the top layer were aspirated and lymphocyte layer was collected using a micropipette. Cells were washed 3 times with PBS, collected in RPMI, and were subjected to experiments.

Harvested splenocyte were cultured at 37° C. and 5% CO2 in RPMI and were either stimulated with S-peptide pool or buffer. After 6 hours, media were collected, cells were washed twice with PBS and incubated for another 12 hours and were considered as 18-hour sample. Samples were collected for cytokine assay and cells were processed for flow cytometric analysis of T cell populations. For day 14 samples, surface antigen and intracellular cytokine staining of cells were performed with following antibodies according to the supplier's instructions: V500-anti-mouse CD45 (BD Bioscience, USA), FITC-anti-mouse CD4 (ThermoFisher, USA), anti-mouse IFN-gamma (ThermoFisher, USA), Alexa Fluor® 594-secondary antibody (ThermoFisher, USA), in-house developed TNF alpha fusion protein, anti Fc primary antibody (ThermoFisher, USA), Alexa Fluor® 594-secondary antibody (ThermoFisher, USA), anti-mouse IL-2 (ThermoFisher, USA), Alexa Fluor® 594-secondary antibody (ThermoFisher, USA), anti-mouse IL-6 (ThermoFisher, USA), Alexa Fluor® 594-secondary antibody (ThermoFisher, USA) and no live/dead staining. Cells were washed, fixed, permeabilized, stained and stored at 4° C. After 48 hours, cell-events were acquired using an FACS Lyric (BD Biosciences), followed by FlowJo software (FlowJo LLC, Ashland, OR) analysis. For day-91 samples, surface antigen and intracellular cytokine staining of cells were performed with following antibodies as per supplier's instructions: V500-anti-mouse CD45 (BD Bioscience, USA), Alexa Fluor® 700-anti-mouse CD3 (BD Bioscience, USA), APC-Cy™7-anti-mouse CD4 (BD Bioscience, USA), PE-Cy™7-anti-mouse CD8 (BD Bioscience, USA), FITC-anti-mouse IFN-γ (BD Bioscience, USA), 88700-anti-mouse TNF-alpha (BD Bioscience, USA), BV421-anti-mouse IL-2 (BD Bioscience, USA), APC-anti-mouse IL-4 (BD Bioscience, USA), PE-anti-mouse IL-17A (BD Bioscience, USA) and no live/dead staining. For memory B cell identification, following antibodies were used: V500 anti-mouse CD45 (BD Bioscience, USA), PE-Cy™7-anti-mouse CD19 (BD Bioscience, USA), BV421-anti-mouse CD27 (BD Bioscience, USA) and no live/dead staining. Cells were washed, fixed/permeabilized, stained and cell-events were acquired using an FACS Lyric (BD Biosciences), followed by FlowJo software (FlowJo LLC, Ashland, OR) analysis.

IL-2 and 11-6 were measured by ELISA using standard protocol. ELISA plate (Corning) was coated with 1 µg/mL IL-2 polyclonal antibody (ThermoFisher, USA) in Dulbecco's phosphate-buffered saline (DPBS) (ThermoFisher, USA) for 2 hours at room temperature. After coating, Plate was washed for 3 times with DPBS+0.05 Tween 20 (Scharlau, Spain) and then blocked with PBS+1% BSA (ThermoFisher, USA)+0.050% Tween 20 for 2 hours at 37° C. After blocking, plates were washed for 3 times and incubated with IL-2 and mouse splenocyte samples for 2 hours at 37° C. Plates were then washed again and incubated with IL-2 monoclonal antibody (ThermoFisher, USA) for 2 hours at 37° C. After washing for 3 times, plates were incubated with Goat anti-Mouse IgG (H+L) HRP-conjugated secondary antibody, (ThermoFisher, USA) for 50 min at room temperature. Final washing was done for 3 times and then developed with Pierce TMB substrate (ThermoFisher, USA) for 10 min. Reaction was stopped with 1N HCl. Signals were measured at 450 nm wavelength within 30 min. For IL-6 analysis, IL-6 Mouse ELISA kit (ThermoFisher, USA) was used, steps were performed as per manufacturer instructions.

Results

Bioinformatics analysis to initiate the designing of 'GBPD060'—The analysis started with alignment of available sequences of SARS-CoV-2 spike (S) protein. A total of 15 D614G sequences out of 170 reference sequences of SARS-CoV-2 were found. Hydropathy profile showed a minor variation in the S protein between D614 and G614 genotypes. Relevant 3D modeling suggested that there might be a higher angular strain on G614 than on the D614, which could affect the stability and atomic distance with the neighboring atoms.

Construction, antigen expression and formulation of 'GBPD060'—The ORF for the SARS-CoV-2 spike protein with G614-translating codon was obtained from a confirmed COVID-19 patient through PCR amplification (Accession No. MT676411.1). Necessary modifications were performed to obtain the desired clone in pET31b vector as described in 'Methods' section. The schematic diagram of the target gene and construction scheme are shown in FIG. 1A. The capped-mRNA with a 130-202 nucleotide residue-long poly A tail was obtained. The mRNA sequence with poly A tail was confirmed by DNA sequencing after reverse transcription (FIG. 1B-1D); Accession No. MWO45214. The IVT process was tuned and validated to obtain the desired mRNA with high yield and quality (FIGS. 1E and 1F). The mRNA was encapsulated in lipid nanoparticle (LNP) ranging from 60-140 nm with a final pH of 7.2 (FIGS. 1G and H).

A pilot study with limited numbers of mice was conducted to identify the suitable mRNA-LNP size for the formulation. mRNA-LNP either smaller than 60 nm or larger than 120 nm did not generate considerable immunological response even with a dose of 10 μg/mouse. To obtain the best process control for dose production, the mRNA-LNP size range used was set at 85±20 nm (FIG. 1*e*). LNP without SARS-CoV-2 S-mRNA was used as placebo.

Local tolerance and toxicity—Control, treatment and placebo groups comprising 3 male mice each were used for local tolerance testing. No detrimental physical consequences of administration were observed such as, local trauma following injection and/or physicochemical actions of the vaccine from local toxicological or pharmacodynamics effects. No sign of erythema or erythredema were observed in muscle tissue section from the site of injection. Complete blood count (CBC) from different groups indicated good health status of mice; all parameters were in the normal physiological range. There were no signs of anemia, infection, inflammation, and bleeding disorder. Liver function tests (LFTs), such as alanine transaminase (ALT) and aspartate aminotransferase (AST) were performed to confirm clinical suspicion of potential liver injury or disease and to distinguish between hepatocellular damage and cholestasis. Blood urea nitrogen (BUN) was tested to evaluate the health of kidneys, such as kidney disease or damage. Data for ALT, AST and BUN were in the normal range and no significant changes were observed between pre-immunization and after immunization.

'GBPD060' induces high and Th-1 biased antibodies against full-length SARS-CoV2 S-protein—Immunization of mice with mRNA-LNP produced specific titer in a dose dependent manner (FIG. 2*a*). Low dose (0.1 μg/mouse) immunization produced a moderate level of antibody response (FIG. 2*a*, Treatment 1). The best antibody response was obtained with 1 μg/mouse dose (FIG. 2*a*, Treatment 2). High dose (10 μg/mouse) immunization produced a higher level of titer with a wide-spread distribution, and therefore, this dose was considered unacceptable (FIG. 2*a*, Treatment 3).

The subtyping analysis revealed that the titer contained a balanced ratio of IgG2a and IgG1 in a 7-day post immunization sera, and it remains stable for 14-day post immunization sera (FIG. 2*b*, Treatment 2). A similar trend was observed for (IgG2a+IgG2b) and (IgG1+IgG3) (FIG. 2*c*, Treatment 2), which has indicated that the antigenic response was CD4+Th1-biased. High dose (10 μg/mouse) injected mice sera also produced similar response (FIGS. 2*b* and *c*, Treatment 3). To check whether the immunization generated antibody pool spanning for the whole antigen or for any specific domain (either S1 or S2), a surface plasmon resonance (SPR) experiment was conducted. The S protein chip recognized high-affinity antibody from the anti-sera pool (FIG. 2*d*). The response was attenuated significantly for S-protein(s) (S, S1 and S2) pretreated sera (FIG. 2*d*). S and S1 pretreatment showed strong inhibitory responses, while S2 pretreatment showed a comparatively moderate inhibitory response. The purified Ig from the pooled anti-sera produced a significantly pronounced response (FIG. 2*e*). The SPR data clearly showed that the vaccination produced a specific antibody pool against the full-length S protein.

Cellular and cytokine responses to 'GBPD060'—The cellular response and induction of specific cytokines in response to vaccination was also characterized after 14 and 91 days of the first immunization. Splenocytes obtained from vaccinated mice were re-stimulated with a library of SARS-CoV-2-S peptide pool. 14 days after first immunization, the stimulated splenocytes generated a significantly higher population of CD4+Th1 cytokine IFN-gamma, IL-2 and TNF-α expressing cells (0.21±0.03, 0.61±256 0.03 and 0.95±0.11, respectively) compared to the placebo treated group (0.06±0.03, 0.18±257 0.07 and 0.52±0.06, respectively) (FIG. 3a-3c.). CD4+Th2 cytokine IL-6-expressing cells were moderately increased in stimulated splenocytes of vaccinated mice compared to the placebo-injected mice (0.42±0.08 and 0.23±0.02, respectively) (FIG. 3d). The amount of secreted cytokines in treated vs. placebo groups were as follows: IFN-gamma (treatment group, 559.87±70.76 pg/ml and 303.47±156.53 pg/ml; placebo, 28.29±2.03 pg/ml and 262 16.04±2.52 pg/ml), IL2 (treatment group, 499.10±30.80 pg/ml and 345.17±22.85 pg/ml; 263 placebo group, 175.71±21.92 pg/ml and 136.87±15.18 pg/ml), IL4 (treatment group, 77.94 264±7.7 pg/ml and 46.36±3.7 pg/ml; placebo group, 22.5±3.25 pg/ml and 9.5±1.08 pg/ml) 265 and IL6 (treatment group, 45.78±15.52 pg/ml and 32.61±15.52 pg/ml; placebo group, 266 16.96±3.53 pg/ml and 14.87±3.08 pg/ml), respectively for 6- and 18-hr, which indicated a vaccine specific response (FIG. 3e-3h).

At 91 days after first immunization, the stimulated (S1 and S2) splenocytes generated a significantly higher population of CD4+Th1 cytokine IFN-γ, TNF-α and IL-2-expressing cells (0.39±0.01 and 0.19±0.08, 0.6±0.17 and 1.13±0.21, and 0.07±0.07 and 0.11±271 0.11, respectively) compares to the placebo treated group (0.14±0.03 and 0.18±0.08, 0.36±272 0.05 and 0.69±0.04, and 0.07±0.07 and 0.06±0.05, respectively) (FIGS. 3i and 3j). Similarly, S1 and S2 stimulated splenocytes also generated a significantly higher population of CD8+Th1 cytokine IFN-γ, TNF-α and IL-2-expressing cells (0.91±0.08 and 0.48±0.27, 275 0.58±0.25 and 1.3±0.21, and 0.3±0.08 and 0.05±0.05, respectively) compared to the placebo treated group (0.24±0.13 and 0.25±0.1, 0.26±0.15 and 0.55±0.16, and 0.03±277 0.03 and 0.03±0.03, respectively) (FIGS. 3k and 3l). S1 and S2 stimulated splenocytes generated moderate CD4+ and CD8+Th2 cytokine IL-4 and IL-17A-expressing cells compared to the placebo-injected mice (FIG. 3i-3l). Higher levels of sustained Th1 specific cytokine response over Th2 specific cytokine suggested a stable and balanced Th1-biased immunologic response after administration of GBPD060' vaccine. S1 stimulated splenocytes generated a significantly higher population of CD19+CD27+ expressing cells (1.57±0.17) compared to the placebo treated group (0.72±0.12) (FIG. 3m).

'GBPD060' induces neutralization of SARS-CoV-2-S pseudo-type viruses—Sera of vaccinated mice inhibited infection of GFP-expressing pseudo-type SARS-CoV-2-S adenovirus in hACE2-expressing HEK293 (ACE2-HEK293) cells in a dose dependent manner (FIG. 4a). A neutralization assay demonstrated that there was a correlation between the intensity of GFP and SARS-CoV-2 specific antibody for vaccinated mice. A higher concentration of SARS-CoV-2 antibody efficiently neutralized the entry of the pseudovirus into the ACE2-HEK293 cell. The IC50 value for GFP-inhibition was found to be significantly higher for the anti-sera (~3 µg/mL) compared to the CR3022, which is an anti-SARS-CoV monoclonal antibody (mAb), and a commercially available polyclonal mouse antibody against S-protein (~7 µg/ml).

In parallel with the GFP analysis, to confirm the virion copy number, real-time PCR was implemented as an orthologous method. Copy number analysis was performed using GoTaq® qPCR master mix (Promega, USA) with primers. A 5-fold serially diluted known concentration of pseudovirus was used for standard curve generation. GoTaq® DNA Polymerase activation was done at 95° C. for 10 minutes. Denaturation was done at 95° C. for 10 seconds, annealing at 51° C. for 30 seconds, extension at 72° C. for 30 seconds for 40 cycles. After completion of PCR cycle, melt curve was done for sample integrity checking. The data showed correlation with the GFP and gene copy analysis (FIG. 4b). HIV1-based SARS-CoV-2-S pseudo type virus infection was also significantly inhibited by 1 µg/mouse dose anti-sera compared to the placebo anti-sera (FIG. 4c, Serum). Either S1 or S2 protein pretreatment nullified the inhibition capacity of anti-sera (FIG. 4c, Serum+S1 and Serum+S2) confirming that the inhibition property for the HIV1-based SARS-CoV-2-S pseudo type virus is related to the vaccination.

It was then determined whether or not the immunization could protect mice from GFP-expressing homotypic pseudo-type adenovirus. Virus was sprayed into the nasopharyngeal space of mice, either in buffer or pretreated with immunized sera. The anti-sera-treated SARS-CoV-2-S adenovirus produced lower copy of virus compared to the buffer-treated virus (FIG. 4d, Treatment 2 and Treatment 1, respectively). The copy number of virus was found to be reduced further from day 2 to day 3 (FIG. 4d, Treatment 4 and Treatment 3, respectively). These data clearly revealed that though the anti-serum exhibited significant inhibitory capacity against viral infection, systemic immune-protection provides enhanced protection. Lower copy number of virus over time indicated that significance of cellular immunity, along with humoral immunity, for efficient viral clearance. The anti-sera treated with S1+S2 protein failed to inhibit SARS-CoV-2-S adenovirus infection in the placebo-injected mice (FIG. 4d, Treatment 5), and confirming that the inhibition and neutralization of the SARS-CoV-2-S pseudo-type virus is correlated with the immunogenic response generated by the GBPD060' vaccine.

The lungs of control- and GBPD060-immunized mice (single-dose, day 14 post-immunization), which were challenged with homotypic SARS-CoV-2 pseudovirus (day-5 post challenge) were collected. GFP-labelled viruses were clearly found spread throughout the lungs of control group mice. Peritracheal viral infection was predominant and suggested that the viral entry pathway is the airways of the lung (FIG. 4e-4g). The immunized mice lungs showed a few viral-spots on day-5 post challenge tissue, which completely disappeared by day-6 of post challenge. No peritracheal viral signal was observed in these lungs (FIG. 4h-4j). The data provided visual and conclusive evidence that GBPD060 immunization neutralizes SARS-COV2 virus and protects against infection by the virus within the lungs.

A transgene comprising a single variation in the S-protein component, i.e. only the G614 variant was also prepared, and used to make an mRNA vaccine as above described. This vaccine exhibited similar protection against infection by SARS-CoV-2.

Discussion

A vaccine targeting the G614 mutant has been developed. The vaccine incorporates the high-expressing spike protein as antigen in a putative perfusion stabilized condition. Comparative design features of 'GBPD060' are shown in Table 1. 'GBPD060' mRNA has features along with the G614-targeted mutation, which are different from other vaccines. The design comprises R452, Y501 and G614 (named 'RYG') in the final construct which is unique compared to any current vaccine. The RYG-variant showed similar biochemical and biological properties to our developed G614 variant. The ribosome binding site, IgE-signal sequence (by replacing the native 13 amino acids from the N-terminal of the SARS-CoV-2 S protein), and the 3' UTR which comprises the 3'UTRs of the alpha and beta globin gene in tandem are features of the vaccine. The vaccine is formulated for delivery in LNPs which are 65-105 nm in size to provide a suitable antibody response. Further, the pH (7.2) of the formulation buffer for the mRNA-LNP vaccine was lower than that in other vaccines to aid in quick release of the cargo from endosomal compartment and protects the mRNA from acid hydrolysis and lysosomal digestion in the intracellular milieu. The vaccine was found to elicit a stable Th1-IgG2-biased antibody response.

'GBPD060' immunization did not produce any noticeable effect for local or systemic toxicity as was primarily evident by the absence of four cardinal signs of inflammation: redness (Latin rubor), heat (calor), swelling (tumor), and pain (dolor). There was no erythema or erythredema as well in any injection site. Vaccination did not significantly alter CBC and blood chemistry indicating the vaccine is safe for use in mammals.

A balanced response between Th1 and Th2 is desired to achieve safe and effective humoral immunity performance. 'GBPD060' produced a well-balanced IgG1 and IgG2 response at 7 days post-immunization, which was maintained in 14th day post-immunization sera, indicating a stable antibody response. GBPD060' also elicited a higher ratio of IgG2 to IgG1 indicating a higher capacity of the antibody pool to clear antigen from the system. The ratio of IgG2a to IgG1, and cytokine-stained CD4+ and CD8+ T cell population showed a Th1-bias response. Since mouse IgG2 is equivalent to human IgG1, 'GBPD060' will elicit effective cellular and humoral response against SARS-CoV-2 in human.

Importantly, 'GBPD060' has elicited a high level of specific antibody with a single immunization, which is comparable with the level of antibody response observed after administration of a 2nd boosting dose in the mRNA vaccine developed by others. Additionally, a significant level of 51 peptide-pool-specific CD27+ memory B cells were observed 91 days following a first immunization. Therefore, GBPD060 provides suitable protection against SARS-CoV-2 in human with a single dose of injection. A single dose for effective immunization against SARS-CoV-2 is highly desirable to achieve mass global vaccination.

TABLE 1

Comparative design features of 'GBPD060'

| Parameter | GBPD060 | Others |
|---|---|---|
| Construct | T7 promoter | T7 promoter[6] |
| | 51 bp 5'-UTR | 5'-UTR[5-6] |
| | Ribosome binding sequence | Not specified |
| | IgE signal peptide in the ORF | ORF[5-8] |
| | L452R, N501Y and D614G mutations | Not in consideration |
| | K986P and V987P mutations | K986P and V987P mutations[5-6] |
| | Modified alpha and beta globin in 3'-UTR | 3'-UTR[5-6] |
| | 130 bp poly A tail | Poly A tail[5], [7] poly(A) tail (100 nucleotides) interrupted by a linker[6] |
| LNP | LNP composition: MC3, DSPC, Cholesterol and DMG-PEG2000 (50:10:38:5:1.5). | LNP composition: ionizable lipid, DSPC, Cholesterol and PEG2000-DMG[7] |
| | Stabilization buffer: 1x PBS, pH 7.2 | Stabilization buffer: HEPES buffer, pH 8.0; [7] |
| | LNP size range: 85 ± 20 nm | LNP Size: ~75 nm[8] and average size 100 nm[32] |
| IgG2a/IgG1 ratio | ~1.0 | ~0.8, [5] 1.6[8] |

The findings clearly demonstrate that 'GBPD060' is safe for in vivo administration, and elicits balanced and stable cellular and humoral response that neutralize SARS-CoV-2 spike protein-mediated infection.

The invention claimed is:

1. A transgene that encodes:
 i) an RNA polymerase promoter recognized by a polymerase of a single-subunit DNA-dependent RNA polymerase (ssRNAP) family;
 ii) a 5' UTR, wherein the 5'-UTR sequence is:

5'-GAATAAGAGAGAAAAGAAGAGTAAGAAGA
   AATATAAGAGCTAGCGGTAC-3'.

iii) a secretory sequence;
 iv) a coronavirus spike protein component, wherein the spike protein component incorporates a variant sequence at amino acid position 614 of a native spike protein or a position that corresponds with the amino acid position at position 614 of the native spike protein, and additionally comprises a variant sequence at one or both of amino acid positions 452 and 501 of the native spike protein, wherein the amino acid position of the variant sequence is determined from a methionine start codon of the native spike protein and wherein the variant sequence at position 452 is L452R, the variant sequence at position 501 is N501Y and the variant sequence at position 614 is D614G; and
 v) a 3' UTR and poly A sequence.

2. The transgene of claim 1, wherein the promoter is selected from a T7 promoter, T3 promoter, Sp6 promoter, mitochondrial RNA polymerase (POLRMT) promoter and chloroplastic ssRNAP promoter.

3. The transgene of claim 1, wherein the promoter is the T7 promoter.

4. The transgene of claim 1, wherein the spike protein component is a full-length SARS-COV2 spike protein or an antigenic fragment thereof.

5. The transgene of claim 4, wherein the antigenic fragment comprises an N-terminal fragment up to at least amino acid position 614 of the spike protein, a C-terminal fragment including the amino acid at position 614 of the spike protein, or an internal fragment incorporating at least the region V595-G614 or the region G614-A647 of the spike protein.

6. The transgene of claim 1, wherein the protein spike component additionally comprises a variant amino acid sequence selected from the group of: T478K, E484K, E484Q, P681R, P681H, K986P and V987P.

7. The transgene of claim 1, comprising an upstream promoter spacer sequence.

8. The transgene of claim 1, wherein the 5'-UTR sequence is a native coronavirus 5'-UTR.

9. The transgene of claim 1, wherein 3'-UTR is a native coronavirus 3'-UTR.

10. The transgene of claim 1, wherein 3'-UTR comprises one or more of the 3'-UTR of alpha-1-globin, beta-globin, c-fos, metallothionein IG, lipoprotein lipase, glutathione peroxidase 4, glutathione peroxidase 3, glutathione peroxidase 2, c-myc, 15-lipoxygenase, and transferrin receptor 2a.

11. The transgene of claim 10, wherein the 3'-UTR comprises the 3'-UTR of at least one of alpha-1-globin and beta-globin.

12. The transgene of claim 1, wherein the secretory sequence is selected form an IgE receptor secretory sequence, erythropoietin secretory sequence, growth hormone secretory sequence, granulocyte colony stimulating factor secretory sequence, fibroblast growth factor secretory sequence, vascular endothelial growth factor secretory sequence, a G-protein coupled receptor secretory sequence, or a modified secretory sequence thereof that retains the ability to cleave from the spike protein component.

13. The transgene of claim 1, comprising a T7 promoter, an IgE receptor secretory sequence, and a 3'-UTR comprising the 3'-UTR of alpha-1-globin and the 3'-UTR of beta-globin.

14. The transgene of claim 1, wherein the spike protein component additionally comprises the variants, K986P and V987P.

15. The transgene of claim 13, wherein the 3'-UTR comprises the nucleotide sequence of SEQ ID NO: 7.

16. A vaccine incorporating a transgene as defined in claim 1 or an mRNA transcript thereof.

17. The vaccine of claim 16, which is an mRNA vaccine, DNA vaccine, subunit vaccine, non-replicating viral vaccine, attenuated viral vaccine or inactivated viral vaccine.

18. The vaccine of claim 17, which is an mRNA vaccine.

19. The vaccine of claim 18, wherein the mRNA comprises a 5'-methylated cap.

20. The vaccine of claim 18, formulated for administration in lipid nanoparticles.

21. The vaccine of claim 18, comprising the mRNA in a buffer combined with lipids in a ratio of 3:1 to 7:1.

22. The vaccine of claim 18, wherein the pH of the formulation is 7.2±0.2.

23. The vaccine of claim 20, wherein the lipid nanoparticles have an average particle size of 85±20 nm.

24. The vaccine of claim 20, wherein the lipid nanoparticles comprise an ionizable cationic lipid, a PEGylated lipid, a phospholipid, and cholesterol.

25. The vaccine of claim 20, wherein the lipid nanoparticles comprise MC3 ([(6Z,9Z,28Z,31Z)-heptatriaconta-6,9,28,31-tetraen-19-yl] 4-(dimethylamino) butanoate), DSPC ([(2R)-2,3-di (octadecanoyloxy) propyl] 2-(trimethylazaniumyl) ethyl phosphate), dimyristoyl-rac-glycero-3-methoxypolyethylene glycol-2000 and cholesterol.

26. The vaccine of claim 25, comprising MC3; DSPC; cholesterol; and DMG-PEG2000 in a molar ratio of 50:10:38.5:1.5.

27. A method of vaccinating a mammal against a coronavirus infection comprising administering to the mammal a vaccine incorporating a transgene as defined in claim 1 or an mRNA transcript thereof.

28. The method of claim 27, wherein the vaccine is an mRNA vaccine formulated in lipid nanoparticles.

29. The method of claim 27, wherein the vaccine is administered at a dosage of 1-300 μg.

30. The method of claim 27, wherein the mammal is a human.

* * * * *

SEQUENCE LISTING

<160> NUMBER OF SEQ ID NOS: 15

<210> SEQ ID NO 1
<211> LENGTH: 19
<212> TYPE: DNA
<213> ORGANISM: Artificial Sequence
<220> FEATURE:
<223> OTHER INFORMATION: nucleotide sequence encoding the T7 promoter

<400> SEQUENCE: 1
taatacgact cactatagg                                                  19

<210> SEQ ID NO 2
<211> LENGTH: 19
<212> TYPE: DNA
<213> ORGANISM: Artificial Sequence
<220> FEATURE:
<223> OTHER INFORMATION: nucleotide sequence encoding the T3 promoter

<400> SEQUENCE: 2
aattaaccct cactaaagg                                                   19

<210> SEQ ID NO 3
<211> LENGTH: 18
<212> TYPE: DNA
<213> ORGANISM: Artificial Sequence
<220> FEATURE:
<223> OTHER INFORMATION: nucleotide sequence encoding the Sp6 promoter

<400> SEQUENCE: 3
atttaggtga cactatag                                                    18

<210> SEQ ID NO 4
<211> LENGTH: 17
<212> TYPE: DNA
<213> ORGANISM: Artificial Sequence
<220> FEATURE:
<223> OTHER INFORMATION: synthesized sequence

<400> SEQUENCE: 4
gcctggctta tcgaaat                                                     17

<210> SEQ ID NO 5
<211> LENGTH: 51
<212> TYPE: DNA
<213> ORGANISM: Artificial Sequence
<220> FEATURE:
<223> OTHER INFORMATION: synthesized sequence

<400> SEQUENCE: 5
gaaataagag agaaaagaag agtaagaaga aatataagag ctagcggtac c              51

<210> SEQ ID NO 6
<211> LENGTH: 18
<212> TYPE: PRT
<213> ORGANISM: Artificial Sequence
<220> FEATURE:
<223> OTHER INFORMATION: synthesized sequence

<400> SEQUENCE: 6

Met Asp Trp Thr Trp Ile Leu Phe Leu Val Ala Ala Ala Thr Arg Val
1               5                   10                  15

His Ser

<210> SEQ ID NO 7
<211> LENGTH: 54
<212> TYPE: DNA
<213> ORGANISM: Artificial Sequence
<220> FEATURE:
<223> OTHER INFORMATION: synthesized sequence

<400> SEQUENCE: 7
atggactgga cctggatcct cttcttggtg gcagcagcca cgcgagtcca ctcc           54

<210> SEQ ID NO 8
<211> LENGTH: 3783
<212> TYPE: DNA
<213> ORGANISM: Artificial Sequence
<220> FEATURE:
<223> OTHER INFORMATION: synthesized sequence

<400> SEQUENCE: 8
cagtgtgtta atcttacaac cagaactcaa ttaccccctg catacactaa ttctttcaca     60
cgtggtgttt attccctga caaagttttc agatcctcag ttttacattc aactcaggac    120

```
ttgttcttac ctttcttttc caatgttact tggttccatg ctatacatgt ctctgggacc      180
aatggtacta agaggtttga taaccctgtc ctaccattta atgatggtgt ttattttgct      240
tccactgaga agtctaacat aataagaggc tggattttg gtactacttt agattcgaag       300
acccagtccc tacttattgt taataacgct actaatgttg ttattaaagt ctgtgaattt      360
caattttgta atgatccatt tttgggtgtt tattaccaca aaaacaacaa agttggatg       420 gaaagtgagt tcagagttta ttctagtgcg aataattgca cttttgaata tgtctctcag      480
cctttcttta tggaccttga aggaaaacag ggtaatttca aaaatcttag ggaatttgtg      540
tttaagaata ttgatggtta ttttaaaata tattctaagc acacgcctat taatttagtg      600
cgtgatctcc ctcagggttt ttcggcttta gaaccattgg tagatttgcc aataggtatt      660
aacatcacta ggtttcaaac tttacttgct ttacatagaa gttatttgac tcctggtgat      720
tcttcttcag gttggacagc tggtgctgca gcttattatg tgggttatct tcaacctagg      780
acttttctat aaaatataa tgaaaatgga accattacag atgctgtaga ctgtgcactt      840
gaccctctct cagaaacaaa gtgtacgttg aaatccttca ctgtagaaaa aggaatctat      900
caaacttcta actttagagt ccaaccaaca gaatctattg ttagatttcc taatattaca      960
aacttgtgcc cttttggtga agtttttaac gccaccagat ttgcatctgt ttatgcttgg     1020
aacaggaaga gaatcagcaa ctgtgttgct gattattctg tcctatataa ttccgcatca     1080
ttttccactt ttaagtgtta tggagtgtct cctactaaat aaatgatct ctgctttact      1140 aatgtctatg cagattcatt tgtaattaga ggtgatgaag tcagacaaat cgctccaggg     1200
caaactggaa agattgctga ttataattat aaattaccag atgatttac aggctgcgtt      1260 atagcttgga attctaacaa tcttgattct aaggttggtg gtaattataa ttacctgtat     1320
agattgttta ggaagtctaa tctcaaacct tttgagagag atatttcaac tgaaatctat     1380
caggccggta gcacaccttg taatggtgtt gaaggtttta attgttactt cctttacaa     1440 tcatatggtt ccaacccac taatggtgtt ggttaccaac catacagagt agtagtactt      1500
tcttttgaac ttctacatgc accagcaact gtttgtggac ctaaaaagtc tactaatttg     1560
gttaaaaaca aatgtgtcaa tttcaacttc aatggtttaa caggcacagg tgttcttact     1620
gagtctaaca aaaagtttct gccttttcca caatttggca gagacattgc tgacactact     1680
gatgctgtcc gtgatccaca gacacttgag attcttgaca ttacaccatg ttcttttggt     1740
ggtgtcagtg ttataacacc aggaacaaat acttctaacc aggttgctgt tctttatcag     1800
ggtgttaact gcacagaagt ccctgttgct attcatgcag atcaacttac tcctacttgg     1860
cgtgtttatt ctacaggttc taatgttttt caaacacgtg caggctgttt aataggggct     1920
gaacatgtca acaactcata tgagtgtgac atacccattg gtgcaggtat atgcgctagt     1980
tatcagactc agactaattc tcctcggcgg gcacgtagtg tagctagtca atccatcatt     2040
gcctacacta tgtcacttgg tgcagaaaat tcagttgctt actctaataa ctctattgcc     2100
atacccacaa attttactat tagtgttacc acagaaattc taccagtgtc tatgaccaag     2160
acatcagtag attgtacaat gtacatttgt ggtgattcaa ctgaatgcag caatctttg      2220 ttgcaatatg gcagttttg tacacaatta aaccgtgctt taactggaat agctgttgaa     2280
caagacaaaa acacccaaga agttttgca caagtcaaac aaatttacaa acaccacca       2340 attaaagatt ttggtggttt taattttca caaatattac cagatccatc aaaaccaagc      2400
aagaggtcat ttattgaaga tctactttc aacaaagtga cacttgcaga tgctggcttc     2460
```

-continued

| | |
|---|---|
| atcaaacaat atggtgattg ccttggtgat attgctgcta gagacctcat ttgtgcacaa | 2520 |
| aagtttaacg gccttactgt tttgccacct ttgctcacag atgaaatgat tgctcaatac | 2580 |
| acttctgcac tgttagcggg tacaatcact tctggttgga cctttggtgc aggtgctgca | 2640 |
| ttacaaatac catttgctat gcaaatggct tataggttta atggtattgg agttacacag | 2700 |
| aatgttctct atgagaacca aaaattgatt gccaaccaat ttaatagtgc tattggcaaa | 2760 |
| attcaagact cactttcttc cacagcaagt gcacttggaa aacttcaaga tgtggtcaac | 2820 |
| caaaatgcac aagctttaaa cacgcttgtt aaacaactta gctccaattt tggtgcaatt | 2880 |
| tcaagtgttt taaatgatat cctttcacgt cttgaccctc tgaggctga agtgcaaatt | 2940 |
| gataggttga tcacaggcag acttcaaagt ttgcagacat atgtgactca acaattaatt | 3000 |
| agagctgcag aaatcagagc ttctgctaat cttgctgcta ctaaaatgtc agagtgtgta | 3060 |
| cttggacaat caaaaagagt tgattttgt ggaaagggct atcatcttat gtccttccct | 3120 |
| cagtcagcac tcatggtgt agtcttcttg catgtgactt atgtccctgc acaagaaaag | 3180 |
| aacttcacaa ctgctcctgc catttgtcat gatggaaaag cacactttcc tcgtgaaggt | 3240 |
| gtctttgttt caaatggcac acactggttt gtaacacaaa ggaattttta tgaaccacaa | 3300 |
| atcattacta cagacaacac atttgtgtct ggtaactgtg atgttgtaat aggaattgtc | 3360 |
| aacaacacag tttatgatcc tttgcaacct gaattagact cattcaagga ggagttagat | 3420 |
| aaatatttta gaatcatac atcaccagat gttgatttag gtgacatctc tggcattaat | 3480 |
| gcttcagttg taaacattca aaaagaaatt gaccgcctca atgaggttgc caagaattta | 3540 |
| aatgaatctc tcatcgatct ccaagaactt ggaaagtatg agcagtatat aaaatggcca | 3600 |
| tggtacattt ggctaggttt tatagctggc ttgattgcca tagtaatggt gacaattatg | 3660 |
| ctttgctgta tgaccagttg ctgtagttgt ctcaagggct gttgttcttg tggatcctgc | 3720 |
| tgcaaatttg atgaagacga ctctgagcca gtgctcaaag gagtcaaatt acattacaca | 3780 |
| taa | 3783 |

<210> SEQ ID NO 9
<211> LENGTH: 3783
<212> TYPE: DNA
<213> ORGANISM: Artificial Sequence
<220> FEATURE:
<223> OTHER INFORMATION: synthesized sequence

<400> SEQUENCE: 9

| | |
|---|---|
| cagtgcgtga acctgaccac cagaacacag ctgcctccag cctacaccaa cagcttcacc | 60 |
| agaggcgtgt actacccga caaggtgttc agatccagcg tgctgcactc tacccaggac | 120 |
| ctgttcctgc ctttcttcag caacgtgacc tggttccacg ccatccacgt gtccggcacc | 180 |
| aatggcacca agagattcga caaccccgtg ctgcccttca cgacggggt gtactttgcc | 240 |
| agcaccgaga gtccaacat catcagaggc tggatcttcg gcaccacact ggacagcaag | 300 |
| acccagagcc tgctgatcgt gaacaacgcc accaacgtgg tcatcaaagt gtgcgagttc | 360 |
| cagttctgca acgaccccctt cctgggcgtc tactaccaca gaacaacaa gagctggatg | 420 |
| gaaagcgagt tccgggtgta cagcagcgcc aacaactgca ccttcgagta cgtgtcccag | 480 |
| cctttcctga tggacctgga aggcaagcag ggcaacttca gaacctgcg cgagttcgtg | 540 |
| ttcaagaaca tcgacggcta cttcaagatc tacagcaagc acacccctat caacctcgtg | 600 |
| cgggatctgc ctcagggctt ctctgctctg gaacccctgg tggatctgcc catcggcatc | 660 |
| aacatcaccc ggtttcagac actgctggcc ctgcacagaa gctacctgac acctggcgat | 720 |

```
agcagctctg gatggacagc tggagccgct gcctactatg tgggatacct gcagcctcgg    780
accttcctgc tgaagtacaa cgagaacggc accatcaccg acgccgtgga ttgtgctctg    840
gatcctctga gcgagacaaa gtgcaccctg aagtccttca ccgtggaaaa gggcatctac    900
cagaccagca acttccgggt gcagcccacc gaatccatcg tgcggttccc caatatcacc    960
aatctgtgcc ccttcggcga ggtgttcaat gccaccagat cgcctctgt gtacgcctgg   1020 aaccggaagc ggatcagcaa ttgcgtggcc gactactccg tgctgtacaa ctccgccagc   1080
ttcagcacct tcaagtgcta cggcgtgtcc cctaccaagc tgaacgacct gtgcttcaca   1140
aacgtgtacg ccgacagctt cgtgatccgg ggagatgaag tgcggcagat tgcccctgga   1200
cagacaggca agatcgccga ctacaactac aagctgcccg acgacttcac cggctgtgtg   1260
attgcctgga acagcaacaa cctggactcc aaagtcggcg gcaactacaa ttacctgtac   1320
cggctgttcc ggaagtccaa tctgaagccc ttcgagcggg acatctccac cgagatctat   1380
caggccggca gcaccccttg taacggcgtg gaaggcttca actgctactt cccactgcag   1440
tcctacggct tccagccaac aaacggcgtg ggctaccagc cttacagagt ggtggtgctg   1500
agcttcgagc tgctgcatgc tcctgccaca gtgtgcggcc ctaagaaaag caccaatctc   1560
gtgaagaaca aatgcgtgaa cttcaacttc aacggcctga ccggcaccgg cgtgctgaca   1620
gagagcaaca gaagttcct gccattccag cagttcggcc gggatatcgc cgataccaca   1680
gatgccgtca gagatcccca gacactggaa atcctggaca tcacccccttg cagcttcggc   1740 ggagtgtctg tgatcacccc tggcaccaac accagcaatc aggtggcagt gctgtaccag   1800
gatgtgaact gtacagaggt gccagtggcc attcacgccg atcagctgac ccctacttgg   1860
cgggtgtact ccacaggcag caatgtgttt cagaccagag ccggctgtct gatcggagcc   1920
gagcacgtga acaatagcta cgagtgcgac atccccatcg gcgctggcat ctgcgcctct   1980
taccagacac agacaaacag ccccagacgg gccagatctg tggccagcca gagcatcatt   2040
gcctacacaa tgtctctggg agccgagaac agcgtggcct actccaacaa ctctatcgct   2100
atccccacca acttcaccat cagcgtgacc acagagatcc tgcctgtgtc catgaccaag   2160
accagcgtgg actgcaccat gtacatctgc ggcgattcca ccgagtgctc caacctgctg   2220
ctgcagtacg gcagcttctg cacccagctg aatagagccc tgacagggat cgccgtggaa   2280
caggacaaga cacccaaga ggtgttcgcc caagtgaagc agatctacaa gacccctcct   2340
atcaaggact cggcggctt caatttcagc cagattctgc ccgatcctag caagcccagc   2400
aagcggagct tcatcgagga cctgctgttc aacaaagtga cactggccga cgccggcttc   2460
atcaagcagt atggcgattg tctgggcgac attgccgcca gggatctgat ttgcgcccag   2520
aagtttaacg gactgacagt gctgcctcct ctgctgaccg atgagatgat cgcccagtac   2580
acatctgccc tgctggccgg cacaatcaca agcggctgga catttggagc tggcgctgcc   2640
ctgcagatcc cctttgctat gcagatggcc taccggttca acggcatcgg agtgacccag   2700
aatgtgctgt acgagaacca gaagctgatc gccaaccagt tcaacagcgc catcggcaag   2760
atccaggaca gcctgagcag cacagcaagc gccctgggaa agctgcagga cgtggtcaac   2820
cagaatgccc aggcactgaa cacccctgtc aagcagctgt ctagcaactt cggagccatc   2880
agctctgtgc tgaacgatat cctgagcaga ctggaccctc tgaggccga ggtgcagatc   2940 gacagactga tcacaggcag actgcagagc ctccagacat acgtgaccca gcagctgatc   3000
agagccgccg agattagagc ctctgccaat ctggccgcca ccaagatgtc tgagtgtgtg   3060
```

| | |
|---|---:|
| ctgggccaga gcaagagagt ggacttttgc ggcaagggct accacctgat gagcttccct | 3120 |
| cagtctgcac cacacggcgt ggtgtttctg cacgtgacct acgtgcccgc tcaagagaag | 3180 |
| aatttcacca ccgctccagc catctgccac gacggcaaag cccactttcc tagagaaggc | 3240 |
| gtgttcgtgt ccaacggcac ccattggttc gtgacacagc ggaacttcta cgagccccag | 3300 |
| atcatcacca ccgacaacac cttcgtgtct ggcaactgcg acgtcgtgat cggcattgtg | 3360 |
| aacaataccg tgtacgaccc tctgcagccc gagctggaca gcttcaaaga ggaactggac | 3420 |
| aagtacttta agaaccacac aagccccgac gtggacctgg gcgatatcag cggaatcaat | 3480 |
| gccagcgtcg tgaacatcca gaaagagatc gaccggctga acgaggtggc caagaatctg | 3540 |
| aacgagagcc tgatcgacct gcaagaactg gggaagtacg agcagtacat caagtggcct | 3600 |
| tggtacatct ggctgggctt tatcgccgga ctgattgcca tcgtgatggt cacaatcatg | 3660 |
| ctgtgttgca tgaccagctg ctgtagctgc ctgaagggct gttgtagctg tggctcctgc | 3720 |
| tgcaagttcg acgaggacga ttctgagccc gtgctgaaag cgtgaagct gcactacacc | 3780 |
| tga | 3783 |

<210> SEQ ID NO 10
<211> LENGTH: 3783
<212> TYPE: DNA
<213> ORGANISM: Artificial Sequence
<220> FEATURE:
<223> OTHER INFORMATION: synthesized sequence

<400> SEQUENCE: 10

| | |
|---|---:|
| cagtgcgtga acctgaccac cagaacacag ctgcctccag cctacaccaa cagcttcacc | 60 |
| agaggcgtgt actaccccga caaggtgttc agatccagcg tgctgcactc tacccaggac | 120 |
| ctgttcctgc ctttcttcag caacgtgacc tggttccacg ccatccacgt gtccggcacc | 180 |
| aatggcacca agagattcga caaccccgtg ctgcccttca cgacggggt gtactttgcc | 240 |
| agcaccgaga agtccaacat catcagaggc tggatcttcg gcaccacact ggacagcaag | 300 |
| acccagagcc tgctgatcgt gaacaacgcc accaacgtgg tcatcaaagt gtgcgagttc | 360 |
| cagttctgca acgacccctt cctgggcgtc tactaccaca agaacaacaa gagctggatg | 420 |
| gaaagcgagt tccgggtgta cagcagcgcc aacaactgca ccttcgagta cgtgtcccag | 480 |
| cctttcctga tggacctgga aggcaagcag ggcaacttca agaacctgcg cgagttcgtg | 540 |
| ttcaagaaca tcgacggcta cttcaagatc tacagcaagc acaccccct caacctcgtg | 600 |
| cgggatctgc ctcagggctt ctctgctctg gaaccctgg tggatctgcc catcggcatc | 660 |
| aacatcaccc ggtttcagac actgctggcc ctgcacagaa gctacctgac acctggcgat | 720 |
| agcagctctg gatggacagc tggagccgct gcctactatg tgggatacct gcagcctcgg | 780 |
| accttcctgc tgaagtacaa cgagaacggc accatcaccg acgccgtgga ttgtgctctg | 840 |
| gatcctctga gcgagacaaa gtgcaccctg aagtccttca ccgtggaaaa gggcatctac | 900 |
| cagaccagca acttccgggt gcagcccacc gaatccatcg tgcggttccc caatatcacc | 960 |
| aatctgtgcc ccttcggcga ggtgttcaat gccaccagat cgcctctgt gtacgcctgg | 1020 |
| aaccggaagc ggatcagcaa ttgcgtggcc gactactccg tgctgtacaa ctccgccagc | 1080 |
| ttcagcacct tcaagtgcta cggcgtgtcc cctaccaagc tgaacgacct gtgcttcaca | 1140 |
| aacgtgtacg ccgacagctt cgtgatccgg ggagatgaag tgcggcagat tgcccctgga | 1200 |
| cagacaggca agatcgccga ctacaactac aagctgcccg acgacttcac cggctgtgtg | 1260 |
| attgcctgga acagcaacaa cctggactcc aaagtcggcg gcaactacaa ttacctgtac | 1320 |

```
cggctgttcc ggaagtccaa tctgaagccc ttcgagcggg acatctccac cgagatctat    1380
caggccggca gcacccttg taacggcgtg aaggcttca actgctactt cccactgcag      1440
tcctacggct tccagccaac aaacggcgtg ggctaccagc cttacagagt ggtggtgctg    1500
agcttcgagc tgctgcatgc tcctgccaca gtgtgcggcc taagaaaag caccaatctc    1560 gtgaagaaca aatgcgtgaa cttcaacttc aacggcctga ccggcaccgg cgtgctgaca   1620
gagagcaaca agaagttcct gccattccag cagttcggcc gggatatcgc cgataccaca   1680
gatgccgtca gagatcccca gacactggaa atcctggaca tcaccccttg cagcttcggc   1740
ggagtgtctg tgatcacccc tggcaccaac accagcaatc aggtggcagt gctgtaccag   1800
ggcgtgaact gtacagaggt gccagtggcc attcacgccg atcagctgac ccctacttgg   1860
cgggtgtact ccacaggcag caatgtgttt cagaccagag ccggctgtct gatcggagcc   1920
gagcacgtga acaatagcta cgagtgcgac atccccatcg gcgctggcat ctgcgcctct   1980
taccagacac agacaaacag ccccagacgg gccagatctg tggccagcca gagcatcatt   2040
gcctacacaa tgtctctggg agccgagaac agcgtggcct actccaacaa ctctatcgct   2100
atccccacca acttcaccat cagcgtgacc acagagatcc tgcctgtgtc catgaccaag   2160
accagcgtgg actgcaccat gtacatctgc ggcgattcca ccgagtgctc caacctgctg   2220
ctgcagtacg gcagcttctg cacccagctg aatagagccc tgacagggat cgccgtggaa   2280
caggacaaga cacccaaga ggtgttcgcc caagtgaagc agatctacaa gacccctcct    2340
atcaaggact cggcggctt caatttcagc cagattctgc ccgatcctag caagcccagc    2400
aagcggagct tcatcgagga cctgctgttc aacaaagtga cactggccga cgccggcttc   2460
atcaagcagt atggcgattg tctgggcgac attgccgcca gggatctgat ttgcgcccag   2520
aagtttaacg gactgacagt gctgcctcct ctgctgaccg atgagatgat cgcccagtac   2580
acatctgccc tgctggccgg cacaatcaca agcggctgga catttggagc tggcgctgcc   2640
ctgcagatcc cctttgctat gcagatggcc taccggttca acggcatcgg agtgacccag   2700
aatgtgctgt acgagaacca gaagctgatc gccaaccagt tcaacagcgc catcggcaag   2760
atccaggaca gcctgagcag cacagcaagc gccctgggaa agctgcagga cgtggtcaac   2820
cagaatgccc aggcactgaa caccctggtc aagcagctgt ctagcaactt cggagccatc   2880
agctctgtgc tgaacgatat cctgagcaga ctggaccctc tgagggccga ggtgcagatc   2940
gacagactga tcacaggcag actgcagagc ctccagacat acgtgaccca gcagctgatc   3000
agagccgccg agattagagc ctctgccaat ctggccgcca ccaagatgtc tgagtgtgtg   3060
ctgggccaga gcaagagagt ggactttgtgc ggcaagggct accacctgat gagcttccct   3120
cagtctgcac cacacggcgt ggtgtttctg cacgtgacct acgtgcccgc tcaagagaag   3180
aatttcacca ccgctccagc catctgccac gacggcaaag cccactttcc tagagaaggc   3240
gtgttcgtgt ccaacggcac ccattggttc gtgacacagc ggaacttcta cgagcccag   3300 atcatcacca ccgacaacac cttcgtgtct ggcaactgcg acgtcgtgat cggcattgtg   3360
aacaataccg tgtacgaccc tctgcagccc gagctggaca gcttcaaaga ggaactggac   3420
aagtacttta gaaccacac aagccccgac gtggacctgg gcgatatcag cggaatcaat   3480
gccagcgtcg tgaacatcca gaaagagatc gaccggctga acgaggtggc caagaatctg   3540
aacgagagcc tgatcgacct gcaagaactg ggaaagtacg agcagtacat caagtggcct   3600
tggtacatct ggctgggctt tatcgccgga ctgattgcca tcgtgatggt cacaatcatg   3660
```

| | |
|---|---:|
| ctgtgttgca tgaccagctg ctgtagctgc ctgaagggct gttgtagctg tggctcctgc | 3720 |
| tgcaagttcg acgaggacga ttctgagccc gtgctgaaag gcgtgaagct gcactacacc | 3780 |
| tga | 3783 |

<210> SEQ ID NO 11
<211> LENGTH: 3783
<212> TYPE: DNA
<213> ORGANISM: Artificial Sequence
<220> FEATURE:
<223> OTHER INFORMATION: synthesized sequence

<400> SEQUENCE: 11

| | |
|---|---:|
| cagtgcgtga acctgaccac cagaacacag ctgcctccag cctacaccaa cagcttcacc | 60 |
| agaggcgtgt actacccga caaggtgttc agatccagcg tgctgcactc tacccaggac | 120 |
| ctgttcctgc ctttcttcag caacgtgacc tggttccacg ccatccacgt gtccggcacc | 180 |
| aatggcacca agagattcga caaccccgtg ctgcccttca cgacggggt gtactttgcc | 240 |
| agcaccgaga agtccaacat catcagaggc tggatcttcg gcaccacact ggacagcaag | 300 |
| acccagagcc tgctgatcgt gaacaacgcc accaacgtgg tcatcaaagt gtgcgagttc | 360 |
| cagttctgca cgaccccctt cctgggcgtc tactaccaca gaacaacaa gagctggatg | 420 |
| gaaagcgagt ccgggtgta cagcagcgcc aacaactgca ccttcgagta cgtgtcccag | 480 |
| cctttcctga tggacctgga aggcaagcag ggcaacttca gaacctgcg cgagttcgtg | 540 |
| ttcaagaaca tcgacggcta cttcaagatc tacagcaagc acacccctat caacctcgtg | 600 |
| cgggatctgc ctcagggctt ctctgctctg gaacccctgg tggatctgcc catcggcatc | 660 |
| aacatcaccc ggtttcagac actgctggcc ctgcacagaa gctacctgac acctggcgat | 720 |
| agcagctctg gatggacagc tggagccgct gcctactatg tgggatacct gcagcctcgg | 780 |
| accttcctgc tgaagtacaa cgagaacggc accatcaccg acgccgtgga ttgtgctctg | 840 |
| gatcctctga gcgagacaaa gtgcaccctg aagtccttca ccgtggaaaa gggcatctac | 900 |
| cagaccagca acttccgggt gcagccccc gaatccatcg tgcggttccc caatatcacc | 960 |
| aatctgtgcc ccttcggcga ggtgttcaat gccaccagat cgcctctgt gtacgcctgg | 1020 |
| aaccggaagc ggatcagcaa ttgcgtggcc gactactccg tgctgtacaa ctccgccagc | 1080 |
| ttcagcacct tcaagtgcta cggcgtgtcc cctaccaagc tgaacgacct gtgcttcaca | 1140 |
| aacgtgtacg ccgacagctt cgtgatccgg ggagatgaag tgcggcagat tgcccctgga | 1200 |
| cagacaggca gatcgccga ctacaactac aagctgcccg acgacttcac cggctgtgtg | 1260 |
| attgcctgga acagcaacaa cctggactcc aaagtcggcg gcaactacaa ttacagatac | 1320 |
| cggctgttcc ggaagtccaa tctgaagccc ttcgagcggg acatctccac cgagatctat | 1380 |
| caggccggca gcacccctg taacggcgtg aaggcttca actgctactt cccactgcag | 1440 |
| tcctacggct tccagccaac atacggcgtg ggctaccagc cttacagagt ggtggtgctg | 1500 |
| agcttcgagc tgctgcatgc tcctgccaca gtgtgcggcc ctaagaaaag caccaatctc | 1560 |
| gtgaagaaca aatgcgtgaa cttcaacttc aacggcctga ccggcaccgg cgtgctgaca | 1620 |
| gagagcaaca agaagttcct gccattccag cagttcggcc gggatatcgc cgataccaca | 1680 |
| gatgccgtca gagatcccca gacactggaa atcctggaca tcacccctg cagcttcggc | 1740 |
| ggagtgtctg tgatcacccc tggcaccaac accagcaatc aggtggcagt gctgtaccag | 1800 |
| ggcgtgaact gtacagaggt gccagtggcc attcacgccg atcagctgac ccctacttgg | 1860 |
| cgggtgtact ccacaggcag caatgtgttt cagaccagag ccggctgtct gatcggagcc | 1920 |

```
gagcacgtga acaatagcta cgagtgcgac atccccatcg gcgctggcat ctgcgcctct    1980
taccagacac agacaaacag ccccagacgg gccagatctg tggccagcca gagcatcatt    2040
gcctacacaa tgtctctggg agccgagaac agcgtggcct actccaacaa ctctatcgct    2100
atccccacca acttcaccat cagcgtgacc acagagatcc tgcctgtgtc catgaccaag    2160
accagcgtgg actgcaccat gtacatctgc ggcgattcca ccgagtgctc caacctgctg    2220
ctgcagtacg gcagcttctg cacccagctg aatagaccc tgacagggat cgccgtggaa    2280
caggacaaga acacccaaga ggtgttcgcc aagtgaagc agatctacaa gacccctcct    2340
atcaaggact cggcggcttc aatttcagc cagattctgc ccgatcctag caagcccagc    2400
aagcggagct tcatcgagga cctgctgttc aacaaagtga cactggccga cgccggcttc    2460
atcaagcagt atggcgattg tctgggcgac attgccgcca gggatctgat ttgcgcccag    2520
aagtttaacg gactgacagt gctgcctcct ctgctgaccg atgagatgat cgcccagtac    2580
acatctgccc tgctggccgg cacaatcaca agcggctgga catttggagc tggcgctgcc    2640
ctgcagatcc ccttttgctat gcagatggcc taccggttca acggcatcgg agtgacccag    2700
aatgtgctgt acgagaacca gaagctgatc gccaaccagt tcaacagcgc catcggcaag    2760
atccaggaca gcctgagcag cacagcaagc gccctgggaa agctgcagga cgtggtcaac    2820
cagaatgccc aggcactgaa caccctggtc aagcagctgt ctagcaactt cggagccatc    2880
agctctgtgc tgaacgatat cctgagcaga ctggaccctc ctgaggccga ggtgcagatc    2940
gacagactga tcacaggcag actgcagagc ctccagacat acgtgaccca gcagctgatc    3000
agagccgccg agattagagc ctctgccaat ctggccgcca ccaagatgtc tgagtgtgtg    3060
ctgggccaga gcaagagagt ggacttttgc ggcaagggct accacctgat gagcttccct    3120
cagtctgcac cacgcggcgt ggtgttcctg cacgtgacct acgtgcccgc tcaagagaag    3180
aatttcacca ccgctccagc catctgccac gacggcaaag cccactttcc tagagaaggc    3240
gtgttcgtgt ccaacggcac ccattggttc gtgacacagc ggaacttcta cgagccccag    3300
atcatcacca ccgacaacac cttcgtgtct ggcaactgcg acgtcgtgat cggcattgtg    3360
aacaataccg tgtacgaccc tctgcagccc gagctggaca gcttcaaaga ggaactggac    3420
aagtacttta agaaccacac aagccccgac gtggacctgg gcgatatcag cggaatcaat    3480
gccagcgtcg tgaacatcca gaaagagatc gaccggctga acgaggtggc caagaatctg    3540
aacgagagcc tgatcgacct gcaagaactg gggaagtacg agcagtacat caagtggcct    3600
tggtacatct ggctgggctt tatcgccgga ctgattgcca tcgtgatggt cacaatcatg    3660
ctgtgttgca tgaccagctg ctgtagctgc ctgaagggct gttgtagctg tggctcctgc    3720
tgcaagttcg acgaggacga ttctgagccc gtgctgaaag gcgtgaagct gcactacacc    3780
tga                                                                 3783
```

<210> SEQ ID NO 12
<211> LENGTH: 1259
<212> TYPE: PRT
<213> ORGANISM: Artificial Sequence
<220> FEATURE:
<223> OTHER INFORMATION: synthesized sequence

<400> SEQUENCE: 12

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser

```
            20                  25                  30
Ser Val Leu His Ser Thr Gln Asp Leu Phe Leu Pro Phe Ser Asn
        35                  40                  45
Val Thr Trp Phe His Ala Ile His Val Ser Gly Thr Asn Gly Thr Lys
    50                  55                  60
Arg Phe Asp Asn Pro Val Leu Pro Phe Asn Asp Gly Val Tyr Phe Ala
65                  70                  75                  80
Ser Thr Glu Lys Ser Asn Ile Ile Arg Gly Trp Ile Phe Gly Thr Thr
                85                  90                  95
Leu Asp Ser Lys Thr Gln Ser Leu Leu Ile Val Asn Asn Ala Thr Asn
            100                 105                 110
Val Val Ile Lys Val Cys Glu Phe Gln Phe Cys Asn Asp Pro Phe Leu
        115                 120                 125
Gly Val Tyr Tyr His Lys Asn Asn Lys Ser Trp Met Glu Ser Glu Phe
        130                 135                 140
Arg Val Tyr Ser Ser Ala Asn Asn Cys Thr Phe Glu Tyr Val Ser Gln
145                 150                 155                 160
Pro Phe Leu Met Asp Leu Glu Gly Lys Gln Gly Asn Phe Lys Asn Leu
                165                 170                 175
Arg Glu Phe Val Phe Lys Asn Ile Asp Gly Tyr Phe Lys Ile Tyr Ser
                180                 185                 190
Lys His Thr Pro Ile Asn Leu Val Arg Asp Leu Pro Gln Gly Phe Ser
            195                 200                 205
Ala Leu Glu Pro Leu Val Asp Leu Pro Ile Gly Ile Asn Ile Thr Arg
            210                 215                 220
Phe Gln Thr Leu Leu Ala Leu His Arg Ser Tyr Leu Thr Pro Gly Asp
225                 230                 235                 240
Ser Ser Ser Gly Trp Thr Ala Gly Ala Ala Tyr Tyr Val Gly Tyr
                245                 250                 255
Leu Gln Pro Arg Thr Phe Leu Leu Lys Tyr Asn Glu Asn Gly Thr Ile
            260                 265                 270
Thr Asp Ala Val Asp Cys Ala Leu Asp Pro Leu Ser Glu Thr Lys Cys
            275                 280                 285
Thr Leu Lys Ser Phe Thr Val Glu Lys Gly Ile Tyr Gln Thr Ser Asn
            290                 295                 300
Phe Arg Val Gln Pro Thr Glu Ser Ile Val Arg Phe Pro Asn Ile Thr
305                 310                 315                 320
Asn Leu Cys Pro Phe Gly Glu Val Phe Asn Ala Thr Arg Phe Ala Ser
                325                 330                 335
Val Tyr Ala Trp Asn Arg Lys Arg Ile Ser Asn Cys Val Ala Asp Tyr
                340                 345                 350
Ser Val Leu Tyr Asn Ser Ala Ser Phe Ser Thr Phe Lys Cys Tyr Gly
            355                 360                 365
Val Ser Pro Thr Lys Leu Asn Asp Leu Cys Phe Thr Asn Val Tyr Ala
        370                 375                 380
Asp Ser Phe Val Ile Arg Gly Asp Glu Val Arg Gln Ile Ala Pro Gly
385                 390                 395                 400
Gln Thr Gly Lys Ile Ala Asp Tyr Asn Tyr Lys Leu Pro Asp Asp Phe
                405                 410                 415
Thr Gly Cys Val Ile Ala Trp Asn Ser Asn Asn Leu Asp Ser Lys Val
            420                 425                 430
Gly Gly Asn Tyr Asn Tyr Leu Tyr Arg Leu Phe Arg Lys Ser Asn Leu
            435                 440                 445
```

```
Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
                660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860
```

```
Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln
    1010                1015                1020

Ser Lys Arg Val Asp Phe Cys Gly Lys Gly Tyr His Leu Met Ser
    1025                1030                1035

Phe Pro Gln Ser Ala Pro His Gly Val Val Phe Leu His Val Thr
    1040                1045                1050

Tyr Val Pro Ala Gln Glu Lys Asn Phe Thr Thr Ala Pro Ala Ile
    1055                1060                1065

Cys His Asp Gly Lys Ala His Phe Pro Arg Glu Gly Val Phe Val
    1070                1075                1080

Ser Asn Gly Thr His Trp Phe Val Thr Gln Arg Asn Phe Tyr Glu
    1085                1090                1095

Pro Gln Ile Ile Thr Thr Asp Asn Thr Phe Val Ser Gly Asn Cys
    1100                1105                1110

Asp Val Val Ile Gly Ile Val Asn Asn Thr Val Tyr Asp Pro Leu
    1115                1120                1125

Gln Pro Glu Leu Asp Ser Phe Lys Glu Glu Leu Asp Lys Tyr Phe
    1130                1135                1140

Lys Asn His Thr Ser Pro Asp Val Asp Leu Gly Asp Ile Ser Gly
    1145                1150                1155

Ile Asn Ala Ser Val Val Asn Ile Gln Lys Glu Ile Asp Arg Leu
    1160                1165                1170

Asn Glu Val Ala Lys Asn Leu Asn Glu Ser Leu Ile Asp Leu Gln
    1175                1180                1185

Glu Leu Gly Lys Tyr Glu Gln Tyr Ile Lys Trp Pro Trp Tyr Ile
    1190                1195                1200

Trp Leu Gly Phe Ile Ala Gly Leu Ile Ala Ile Val Met Val Thr
    1205                1210                1215

Ile Met Leu Cys Cys Met Thr Ser Cys Cys Ser Cys Leu Lys Gly
    1220                1225                1230

Cys Cys Ser Cys Gly Ser Cys Cys Lys Phe Asp Glu Asp Asp Ser
    1235                1240                1245

Glu Pro Leu Lys Gly Val Lys Leu His Tyr Thr
    1250                1255
```

<210> SEQ ID NO 13
<211> LENGTH: 1260
<212> TYPE: PRT
<213> ORGANISM: Artificial Sequence
<220> FEATURE:
<223> OTHER INFORMATION: synthesized sequence

<400> SEQUENCE: 13

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
```

```
              370                 375                 380
Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                    405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
        610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
                660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
        770                 775                 780

Gly Gly Phe Asn Phe Ser Gln Ile Leu Pro Asp Pro Ser Lys Pro Ser
785                 790                 795                 800
```

```
Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
            850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln
            1010                1015                1020

Ser Lys Arg Val Asp Phe Cys Gly Lys Gly Tyr His Leu Met Ser
            1025                1030                1035

Phe Pro Gln Ser Ala Pro His Gly Val Val Phe Leu His Val Thr
            1040                1045                1050

Tyr Val Pro Ala Gln Glu Lys Asn Phe Thr Thr Ala Pro Ala Ile
            1055                1060                1065

Cys His Asp Gly Lys Ala His Phe Pro Arg Glu Gly Val Phe Val
            1070                1075                1080

Ser Asn Gly Thr His Trp Phe Val Thr Gln Arg Asn Phe Tyr Glu
            1085                1090                1095

Pro Gln Ile Ile Thr Thr Asp Asn Thr Phe Val Ser Gly Asn Cys
            1100                1105                1110

Asp Val Val Ile Gly Ile Val Asn Asn Thr Val Tyr Asp Pro Leu
            1115                1120                1125

Gln Pro Glu Leu Asp Ser Phe Lys Glu Glu Leu Asp Lys Tyr Phe
            1130                1135                1140

Lys Asn His Thr Ser Pro Asp Val Asp Leu Gly Asp Ile Ser Gly
            1145                1150                1155

Ile Asn Ala Ser Val Val Asn Ile Gln Lys Glu Ile Asp Arg Leu
            1160                1165                1170

Asn Glu Val Ala Lys Asn Leu Asn Glu Ser Leu Ile Asp Leu Gln
            1175                1180                1185

Glu Leu Gly Lys Tyr Glu Gln Tyr Ile Lys Trp Pro Trp Tyr Ile
            1190                1195                1200
```

-continued

```
Trp Leu Gly Phe Ile Ala Gly Leu Ile Ala Ile Val Met Val Thr
    1205                1210                1215

Ile Met Leu Cys Cys Met Thr Ser Cys Cys Ser Cys Leu Lys Gly
    1220                1225                1230

Cys Cys Ser Cys Gly Ser Cys Cys Lys Phe Asp Glu Asp Asp Ser
    1235                1240                1245

Glu Pro Val Leu Lys Gly Val Lys Leu His Tyr Thr
    1250                1255                1260

<210> SEQ ID NO 14
<211> LENGTH: 1260
<212> TYPE: PRT
<213> ORGANISM: Artificial Sequence
<220> FEATURE:
<223> OTHER INFORMATION: synthesized sequence

<400> SEQUENCE: 14

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300
```

```
Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
            325                 330                 335

Val Tyr Ala Trp Asn Arg Lys Arg Ile Ser Asn Cys Val Ala Asp Tyr
        340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Arg Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
        595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
```

```
                    725                 730                 735
Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
            850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln
        1010                1015                1020

Ser Lys Arg Val Asp Phe Cys Gly Lys Gly Tyr His Leu Met Ser
        1025                1030                1035

Phe Pro Gln Ser Ala Pro His Gly Val Val Phe Leu His Val Thr
        1040                1045                1050

Tyr Val Pro Ala Gln Glu Lys Asn Phe Thr Ala Pro Ala Ile
        1055                1060                1065

Cys His Asp Gly Lys Ala His Phe Pro Arg Glu Gly Val Phe Val
        1070                1075                1080

Ser Asn Gly Thr His Trp Phe Val Thr Gln Arg Asn Phe Tyr Glu
        1085                1090                1095

Pro Gln Ile Ile Thr Thr Asp Asn Thr Phe Val Ser Gly Asn Cys
        1100                1105                1110

Asp Val Val Ile Gly Ile Val Asn Asn Thr Val Tyr Asp Pro Leu
        1115                1120                1125

Gln Pro Glu Leu Asp Ser Phe Lys Glu Glu Leu Asp Lys Tyr Phe
        1130                1135                1140
```

```
Lys Asn His Thr Ser Pro Asp Val Asp Leu Gly Asp Ile Ser Gly
    1145            1150            1155

Ile Asn Ala Ser Val Val Asn Ile Gln Lys Glu Ile Asp Arg Leu
    1160            1165            1170

Asn Glu Val Ala Lys Asn Leu Asn Glu Ser Leu Ile Asp Leu Gln
    1175            1180            1185

Glu Leu Gly Lys Tyr Glu Gln Tyr Ile Lys Trp Pro Trp Tyr Ile
    1190            1195            1200

Trp Leu Gly Phe Ile Ala Gly Leu Ile Ala Ile Val Met Val Thr
    1205            1210            1215

Ile Met Leu Cys Cys Met Thr Ser Cys Cys Ser Cys Leu Lys Gly
    1220            1225            1230

Cys Cys Ser Cys Gly Ser Cys Cys Lys Phe Asp Glu Asp Asp Ser
    1235            1240            1245

Glu Pro Val Leu Lys Gly Val Lys Leu His Tyr Thr
    1250            1255            1260

<210> SEQ ID NO 15
<211> LENGTH: 396
<212> TYPE: DNA
<213> ORGANISM: Artificial Sequence
<220> FEATURE:
<223> OTHER INFORMATION: synthesized sequence

<400> SEQUENCE: 15
caccaccacc accaccactg actcgaggct ggagcctcgg tggccatgct tcttgcccct      60
tgggcctccc cccagcccct cctccccttc ctgcaccegt accccgggt  ctttgagatc     120 tggttaccac taaaccagcc tcaagaacac ccgaatggag tctctaagct acataatacc    180
aacttacact ttacaaaatg ttgtccccca aaatgtagcc attcgtatct gctccgttgc    240
caaagaaagt ttcttcacat tctaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaggc                              396
```